(12) United States Patent
Hidas

(10) Patent No.: US 10,130,293 B2
(45) Date of Patent: Nov. 20, 2018

(54) APPARATUS, SYSTEM AND METHOD FOR MEASURING URINE FLOW AND/OR QUANTITY

(71) Applicant: KESEM HEALTH PTY LTD, Victoria (AU)

(72) Inventor: Gil Hidas, Victoria (AU)

(73) Assignee: KESEM HEALTH PTY LTD., Oakleigh South, Victoria (AU)

( * ) Notice: Subject to any disclaimer, the term of this patent is extended or adjusted under 35 U.S.C. 154(b) by 0 days.

(21) Appl. No.: 15/310,989

(22) PCT Filed: May 12, 2015

(86) PCT No.: PCT/IB2015/053478
§ 371 (c)(1),
(2) Date: Nov. 14, 2016

(87) PCT Pub. No.: WO2015/173726
PCT Pub. Date: Nov. 19, 2015

(65) Prior Publication Data
US 2017/0086728 A1    Mar. 30, 2017

Related U.S. Application Data

(60) Provisional application No. 61/991,695, filed on May 12, 2014.

(51) Int. Cl.
*G01F 1/66* (2006.01)
*A61B 5/20* (2006.01)
(Continued)

(52) U.S. Cl.
CPC ............ *A61B 5/208* (2013.01); *A61B 5/0022* (2013.01); *A61B 5/6887* (2013.01); *A61B 5/743* (2013.01);
(Continued)

(58) Field of Classification Search
CPC ... G01F 1/075; G01F 1/66; A61B 5/20; A61B 5/0022; A61B 5/743
See application file for complete search history.

(56) References Cited

U.S. PATENT DOCUMENTS 6,079,280 A    6/2000    Miller et al.
6,479,727 B1 *  11/2002    Roe ........................ A61F 13/42
                                                                600/306
(Continued)

FOREIGN PATENT DOCUMENTS

DE    3007855 A1    9/1981
JP    H09220216 A    8/1997
(Continued)

*Primary Examiner* — Jewel V Dowtin
(74) *Attorney, Agent, or Firm* — Browdy and Neimark, P.L.L.C.

(57) ABSTRACT

An apparatus for measuring at least one measure related to urination of an individual such as urine flow rate and/or urine quantity. The apparatus is configured to produce acoustic and/or electromagnetic signals indicative of the at least one urination measure upon having urine applied thereover. The invention also provides systems and methods that detect the acoustic and/or electromagnetic signals originating from the apparatus being used by the individual and analyze the detected signals to calculate the at least one measure therefrom by using a designated application module operable via an end device using acoustic sensing means or data receiving means of the end device for detecting the acoustic and/or electromagnetic signals.

30 Claims, 18 Drawing Sheets

(51) Int. Cl.
*A61B 5/00* (2006.01)
*A61B 10/00* (2006.01)
*G01F 1/075* (2006.01)

(52) U.S. Cl.
CPC ............ *A61B 10/007* (2013.01); *G01F 1/075* (2013.01); *G01F 1/66* (2013.01); *G01F 1/666* (2013.01); *A61B 2562/0204* (2013.01); *A61B 2562/0223* (2013.01)

(56) References Cited

U.S. PATENT DOCUMENTS

| | | | |
|---|---|---|---|
| 6,582,379 B1 | 6/2003 | Stisen | |
| 7,416,542 B2* | 8/2008 | Aundal | A61B 5/208 600/419 |
| 2004/0100376 A1* | 5/2004 | Lye | A61B 5/411 340/539.12 |
| 2005/0256428 A1 | 11/2005 | Aundal | |
| 2007/0123778 A1* | 5/2007 | Kantorovich | A61B 5/204 600/437 |
| 2008/0312538 A1* | 12/2008 | Shahar | A61B 5/208 600/459 |
| 2011/0265576 A1* | 11/2011 | Cha | A61B 5/208 73/700 |
| 2015/0157512 A1* | 6/2015 | Abir | A61F 13/42 340/573.5 |
| 2016/0029942 A1* | 2/2016 | Paulsen | A61B 5/208 702/19 |
| 2016/0220079 A1* | 8/2016 | Abir | A47K 11/06 |

FOREIGN PATENT DOCUMENTS

| | | |
|---|---|---|
| JP | H09248289 A | 9/1997 |
| WO | 2009143113 A1 | 11/2009 |

* cited by examiner

MAN

WOMAN

| Date | Time | Volume | Intake | Qmax | Voiding Time | Flow Time | Avg Flow | TQMax |
|---|---|---|---|---|---|---|---|---|
| 5/05/2015 (6) | | | | | | | | |
| 5/05/2015 | 20:37 | 1364 | 440 | | | | | |
| 5/05/2015 | 18:11 | 150 | | 21 | 45 | 45 | 15 | 10 |
| 5/05/2015 | 16:10 | 120 | 220 | | | | | |
| 5/05/2015 | 12:45 | 270 | | 15 | 33 | 31 | 15 | 5 |
| 5/05/2015 | 10:48 | 220 | | 20 | 45 | 45 | 15 | 6 |
| 5/05/2015 | 9:24 | 290 | | 17 | 45 | 45 | 15 | 9 |
| 5/05/2015 | 7:35 | | 220 | 18 | 45 | 45 | 15 | 7 |
| 5/05/2015 | 7:26 | 314 | | 21 | 45 | 45 | 15 | 10 |

Fig. 11

APPARATUS, SYSTEM AND METHOD FOR MEASURING URINE FLOW AND/OR QUANTITY

CROSS-REFERENCE TO RELATED PATENT APPLICATIONS

This application claims priority from U.S. provisional patent application No. 61/991,695 filed on May 12, 2014, which is incorporated herein by reference in its entirety.

FIELD OF THE INVENTION

The present invention generally relates to apparatuses, systems and for monitoring voiding of an individual and more particularly to apparatuses, systems and methods for measuring urine volume or other quantitative measures and/or urine flow.

BACKGROUND OF THE INVENTION

Patent publication no, U.S. Pat. No. 3,363,619 A describes the production of an ink audiogram by means of recording the sound made by voiding urine. In the voiding audiograms, the energy is represented as sound intensity or decibels which are plotted along the Y axis herein and the time of voiding is plotted along the X axis.

Patent publication no. WO2009143113 teaches systems and methods for assessing lower urinary tract function from urinary flow data via sound analysis and user-provided information regarding the lower urinary tract symptoms (LUTS) of frequency, urgency and urge incontinence. Embodiments of the LUTS assessment systems include a computer and a telephone or a digital recording mechanism to capture the sound of one or more urination events, which are stored as audio files in a database. The LUTS assessment systems may include sound analysis software for analyzing the strength and duration of each urination event and may include a web-based software application for viewing the results via the Internet or other network.

U.S. Pat. No. 7,811,237 teaches systems for and methods of assessing urinary flow rate via sound analysis. Embodiments of the uroflow measurement systems include a computer and a telephone or a digital recording mechanism to capture the sound of one or more urination events, which are stored as audio files in a database. The uroflow measurement systems may include sound analysis software for analyzing the strength and duration of each urination event and may include a web-based uroflow software application for viewing the results via the Internet or other network In one embodiment, the sound analysis software performs the steps of reading in the raw data of a selected audio file, generating a plot of the audio signal amplitude vs. time, generating a plot of smoothed data for the purpose of presenting an outline of the flow, generating a main flow plot, which is a plot of the largest continuous flow that has a strength that is greater than a predetermined minimum, and generating a set of numerical values that correspond to the strength and duration of urination.

U.S. Pat. No. 8,567,258 teaches systems and methods that use the unique characteristic of sounds produced as urine is applied over the surface of the water to monitor men's urinary flow patterns and their dynamics. By detecting the intensity at selected acoustic frequencies, it is possible to accurately and precisely measure the urine flow rate. Techniques for analyzing urine flow and its dynamics employ sound levels that are detected with digital filters at two or more distinct frequency regions or channels of the sound spectrum. One frequency region that is designated the measurement channel is where the sound measurement intensity strongly depends on urine flow levels. Another frequency region that is designated the reference channel is where the sound measurement intensity is not dependent on urine flow levels. By using a combination of measurements from the measurement channel and the reference channel, the urine flow monitoring apparatus compensates for variations in operating conditions and other factors.

U.S. Pat. No. 5,078,012 teaches a method and apparatus for measuring uroflow parameters by flow impulse momentum, providing measurement and print out in real time of such parameters as the flow rate curve and of maximum flow rate, average flow rate, voided volume, voiding time, flow time, and time to maximum flow rate, necessary for medical diagnosis.

U.S. Pat. No. 5,807,278 teaches a noninvasive bladder pressure and urinary flow measurement apparatus and method, the apparatus including a pressure cuff configured to be removably mounted to the penis of the patient and an inflation system for selectively inflating and deflating the pressure cuff.

US application publication no. US20120123233 A1 describes a handheld USB Cup for use in collection of a fluidic body sample, comprising a receptacle comprising side surfaces, a bottom plate and a sensor assembly, the sensor assembly comprising at least one sensor and a slave circuitry; said sensor assembly is permanently affixed to said side surfaces or said bottom plate. The receptacle is capable of maintaining the fluidic body sample for a sufficient time period in the vicinity of the sensor thereby the sensor is operative to provide continuous measurement of an electric, chemical or physical property of the urine.

SUMMARY OF THE INVENTION

The present invention provides an apparatus for measuring at least one measure related to urination of an individual being configured to produce acoustic and/or electromagnetic signals indicative of at least one urination measure upon having urine applied thereover.

According to some embodiments of the apparatus, the apparatus comprises an acoustic plate configured for vibrating in response to the urine flowing thereover. The acoustic plate optionally comprises an acoustic membrane.

The acoustic plate may be held in the apparatus in a tilted manner in respect to the direction of gravity to also direct the urine to flow therefrom.

According to some embodiments of the apparatus, the apparatus further comprises a collecting container configured for hanging over the toilet bowl or seat, for collecting urine for quantitative measuring thereof and/or for improving acoustics of the acoustic plate. The container optionally comprises an indicator for indicating a measure related to the volume of the urine therein.

According to some embodiments of the apparatus, the apparatus comprises at least one holder for hanging over a toilet bowl or toilet seat.

According to some embodiments of the apparatus, the apparatus comprises: a body configured for hanging over a toilet seat or bowl; a mechanical sensing device for mechanically measuring urine flow and/or urine quantity, the body being configured to direct urine therefrom into the mechanical sensing device; and at least one means for producing acoustic signals indicative of the measured flow or quantity during a urination session. In these embodiments, the apparatus is configured as such to mechanically produce an electromagnetic signal indicative of a known quantity of urine whenever such quantity is measured thereby. For example, the mechanical sensing device comprises a paddlewheel sensor, configured for producing an electromagnetic signal upon full or partial rotation of a wheel thereof caused by urine flow thereover, said signal being indicative of a known urine volume rate.

According to some embodiments of the apparatus, the body of the apparatus further comprises and holds thereby an acoustic plate for improving urine flow sound, said plate also being configured to direct urine into said mechanical sensing device.

According to other embodiments of the apparatus, the apparatus comprises a transducer sensor and plate attached thereto configure for sensing urination related vibrations and transforming these vibrations into electronic signals. The apparatus according to these embodiments further comprises communication means for transmitting the signals outputted by said transducer sensor to a remote end device for processing thereof for measuring urine flow rate and/or urine quantity therefrom.

The present invention further provides a system for measuring at least one measure related to urination of an individual comprising: an apparatus configured to produce acoustic signals indicative of said at least one urination measure upon having urine applied thereover; and an application module operable via an end device, the application module being configured to detect acoustic signals originating from said apparatus and calculate the at least one measure related to urine flow and/or urine quantity therefrom, wherein the application is adapted to use acoustic sensing means and processing means of the end device via which it operates.

According to some embodiments of the system, the application module is further configured to record the acoustic signals for offline processing thereof.

According to some embodiments of the system, the application module is configured to calculate at least one of the following measures: urination flow rate, urination flow rate behavior, urination volume, depending on the type and configuration of the apparatus being used.

According to some embodiments of the system, the application module is configured for adapting its calculations and measures to the type of apparatus being used by having a user interface allowing individuals to select the apparatus type at use.

According to some embodiments of the system, the types of apparatuses comprise: acoustic plate apparatus comprising an acoustic plate configured for improving acoustics of urine flow for urine flow rate and flow rate behavior measuring; acoustic plate combined with a collection container for both flow rate and volume measuring; a volume measuring apparatus comprising a directing bowl shaped body and a mechanical sensing device configured for direct urine quantity measuring, which produces an indication electric signal upon sensing a known quantity of urine for the application to detect thereof; a combined apparatus comprising the volume measuring apparatus and the acoustic plate placed thereover for flow and volume measuring.

According to some embodiments of the system, the mechanical sensing device comprises a paddlewheel sensing device having a wheel of blades rotatable about an axis upon application of urine thereof and one or more magnets rotatable by the wheel for producing electromagnetic signals (through the Hall effect), the signals being indicative of a known urine volume rate, wherein the bowl shaped body being configured to direct the urine to flow into said wheel.

According to some embodiments of the system, the application module is further configured to indicate the measured or calculated parameters using display means of the end device.

According to some embodiments of the system, the application module is further configured to transmit the measured or calculated data to a remote end device.

According to some embodiments of the system, the application module is further configured to record the measuring of multiple urination sessions of each individual via a designated voiding diary for monitoring urination behavior of the individual over time. For example, the application module analyzes the recorded diary data over time for identifying urination related conditions of the individual and alerts the individual and/or other individuals or entities regarding urination related alerting conditions identified by the application module.

The present invention further provides a method for measuring at least one measure related to urination of an individual comprising: detecting acoustic signals indicative of urine applied over an apparatus configured for producing the acoustic signals indicative of the at least one urination measure upon having urine applied thereover, using for the detection a designated application module operated via an end device used by the urinating individual to detect the signals through the end device's acoustic sensing means; analyzing the acoustic signals using said application module to calculate said at least one measure from the detected acoustic signals; outputting and/or storing data indicative of the calculated at least one measure.

According to some embodiments of the method, the method further comprises recording said detected acoustic signals for offline analysis thereof.

According to some embodiments of the method, the analysis is adaptable by the application module to the type of apparatus being used.

According to some embodiments of the method, the at least one measure comprises at least one of: urine flow rate, urine flow rate behavior, urine quantity.

According to some embodiments of the method, the apparatus is configured for at least one of: measuring urine flow rate by improving acoustics of urine applied thereover; directly measuring urine volume.

According to some embodiments of the method, for flow rate measuring the analysis process comprises: spectral envelope filtering of the detected acoustic signal resulting in a time-domain signal; decimation and low-pass filtering of the time domain signal; Log based scaling of the envelope; additional low-pass filtering; and de-convolution.

According to some embodiments of the method, the method further comprises recording measured parameters during multiple urination sessions of each individual via a designated voiding diary for monitoring urination behavior of the individual over time. The method may also include analyzing the recorded diary data over time for identifying urinary related conditions of the individual and alerting the individual and/or other individuals or entities regarding urinary conditions identified by the application module.

BRIEF DESCRIPTION OF THE DRAWINGS

FIG. 4A shows the apparatus over the toilet bowl in a position that is suitable for urination for male subjects; and FIG. 4B shows the apparatus over the toilet bowl with the toilet seat covering thereof, in a position that is suitable for female subjects.

FIG. 5A shows an upper view of the apparatus and toilet; and FIG. 5B shows transparent side view of the apparatus and toilet.

FIG. 6A shows an upper view of the apparatus and toilet; and FIG. 6B shows transparent side view of the apparatus and toilet.

FIG. 11 shows Uroflow output table indicative of follow up on volume of urine samples for different measurement sessions.

FIG. 12A shows the entire processing flow; and FIG. 12B shows a de-convolution process for non-linear compensation.

FIG. 16A shows an elevated perspective view of the apparatus; and FIG. 16B shows a side view of the apparatus.

DETAILED DESCRIPTION OF SOME EMBODIMENTS OF THE INVENTION

Figure 1:
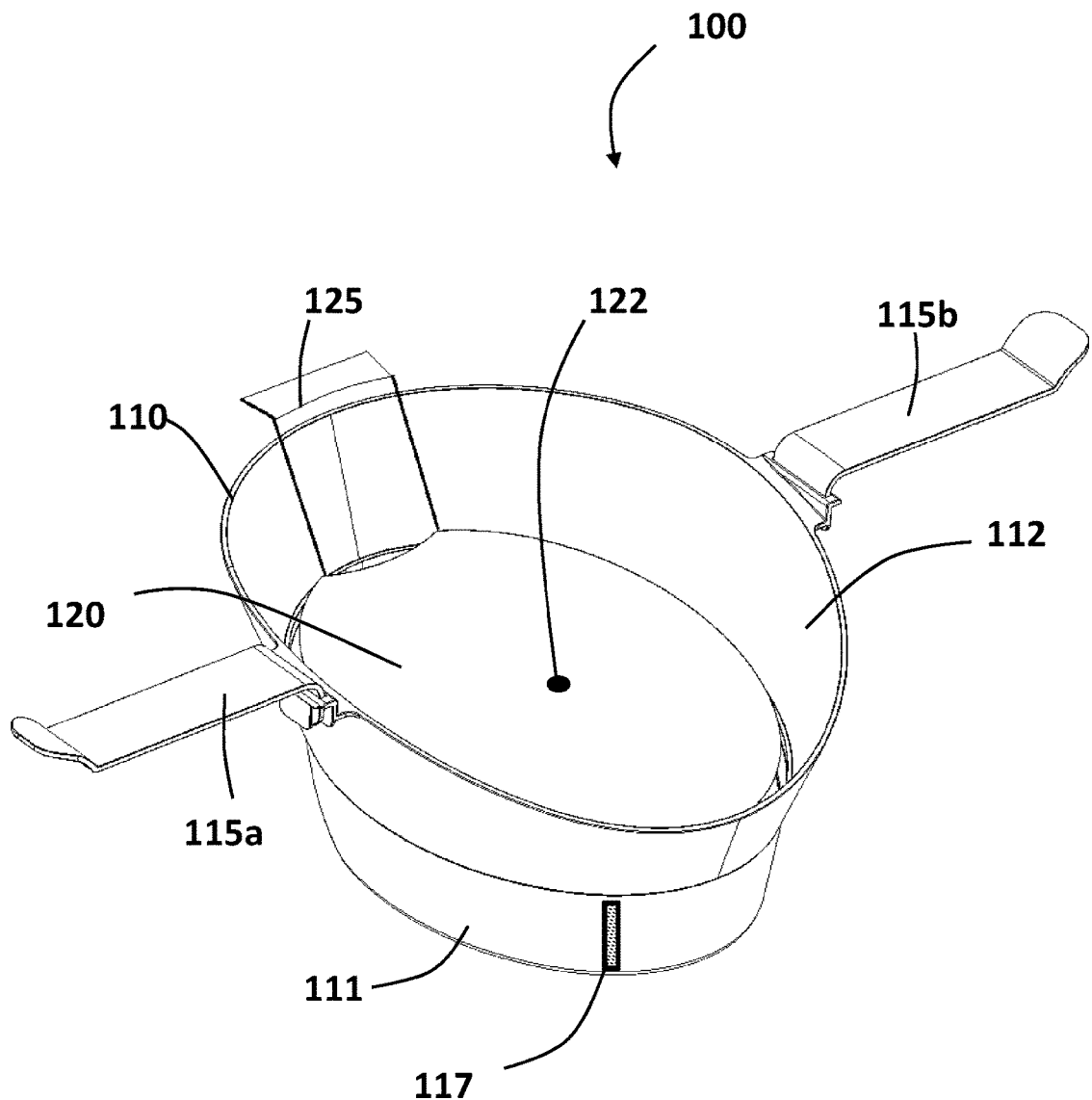
FIG. 1 shows a perspective upper view of an apparatus for collecting urine and for improving acoustics of urine flow sound for urine flow and optionally also urine volume measuring, according to some embodiments of the present invention.

In the following detailed description of various embodiments, reference is made to the accompanying drawings that form a part thereof, and in which are shown by way of illustration specific embodiments in which the invention may be practiced. It is understood that other embodiments may be utilized and structural changes may be made without departing from the scope of the present invention.

The present invention provides apparatuses, systems and methods for measuring urine flow rate or quantity (e.g. volume and/or weight) using sound detection. According to some embodiments, the apparatus is configured for directing urine as well as for improving sound detection of the urine as it flows and/or for direct measuring of urine quantity.

The system of the present invention includes one or more apparatuses designed to be placed over the toilet seat or bowl and configured to improve acoustics of the urination when directed towards the toilet bowl or a collecting bowl (container) and/or to directly measure the urine volume or any other quantity related measure; and a software module operable via users end devices designed to use at least acoustic sensing means (e.g. microphone) of the end device for receiving signals indicative of the urination flow and/or quantity in each urination session. The application us programmed to process data/signals received from the device's acoustic sensing means and to calculate therefrom one or more urination related parameters such as volume and/or flow rate during the urination session timeframe and/or flow rate changes during the urination session timeframe. The processing of course depends on the apparatus being used.

In some embodiments, the apparatus comprises an acoustic plate simply placed over the toilet bowl or seat that vibrates in response to appliance of urine thereover. This acoustic plate is designed to improve sound of the urine flow for improved measuring of the urine flow. The improvement may be manifested in simple amplitude amplification and/or by improving signal-to-noise detection and/or improving spectral separation.

According to some embodiments, the designated software application is configured for continuously recording the urine flow sound during urination and analyzing sound data indicative thereof for calculating the urine flow rate, changes in urine flow rate and/or urine volume.

According to some embodiments, the apparatus includes a container designed to collect the urine therein and the above discussed acoustic plate, which may be an acoustic membrane, placed over the upper opening of the collection container such that a space is formed between the surface of the acoustic plate and the bottom of the container. The acoustic plate may be configured for directing the urine liquid into the container and for improving acoustics of the urine flow sound when impacting the surface of the plate. According to some embodiments, the apparatus is further configured for hanging over the toilet seat or toilet bowl edge.

According to some embodiments, the plate is held over the container such that it is tilted in respect to the floor surface perpendicular to gravitational force, when the apparatus is placed over the toilet bowl or seat for directing the urine into the container. In this configuration the surface of the plate is maintained substantially empty of liquid during the urination (depending on flow rate) for optimizing the sound quality at the moment of impact of the urine against the plate during urination.

In some embodiments, the container is also configured for measuring the overall volume of the urine collected thereby. The measuring can be done manually by the individual, e.g. in cases in which the container includes a measuring scale therein allowing the individual to read the urine volume from or automatically by using any known in the art sensor or technique to measure fluid volume such as weight sensors that allow deducing the urine volume from the urine weight e.g. transducer sensors for weight or pressure measuring, mechanical volume sensors such as turbine or paddle wheel meters and the like.

The application of the system of the present invention, in some embodiments thereof, is designed to be operated through a mobile device such as smartphone, tablet device, laptop and the like. The sound of urine impacting the plate of the apparatus is recorded by using an audio sensor of the mobile device such as a microphone.

In some embodiments, the sound of urine impacting the plate of the apparatus is detected by using an audio sensor such as a separate microphone or other transducer, such as piezoelectric embedded in the apparatus. The detected audio signals can be transmitted to the mobile device wirelessly or via a wire connection e.g. by connecting the apparatus to the headphone jack of the mobile device via a cable.

According to some embodiments, the recorded audio signals are then provided as an input for an analysis algorithm of the application configured to analyze the recorded signals of the urine by using a process enabling identification of periodicities of the urine flow. The output of this process is the flow rate of the urine over time during the urination session e.g. in volume units per time units (for example ml/sec).

According to other embodiments, the apparatus includes a sensor for directly sensing urine quantity such as a paddlewheel sensing device which senses urine volume and may include a wheel having multiple paddles (wings) rotatable by the flow of the urine directed therethrough. The sensor also includes means for producing indication sound upon each one or more turning of its wheel to allow the application to measure the volume of the urine by simply identifying each indication sound during the urination session and counting the number of indications produced therethrough, each wheel spin being indicative of the volume of urine passing therethrough.

According to some embodiments of the invention, there is provided a method for measuring urine flow and/or urine quantity of an individual within a urination session by receiving a urination related sound data which is either recorded or arriving in real time from the end device's acoustic sensing means, while the individual urinates over the acoustic plate of the measuring apparatus; optionally also receiving the volume of the overall urine quantity; and processing the received data to output data indicative of the urine flow rate. In some embodiments, the analysis is done using spectral envelope filtering of the sound signal data, decimation and low-pass filtering, log-base scaling of the signal envelope for first order correction, optionally additional low-pass filtering and special non-linear compensation such as de-convolution.

Figure 2:
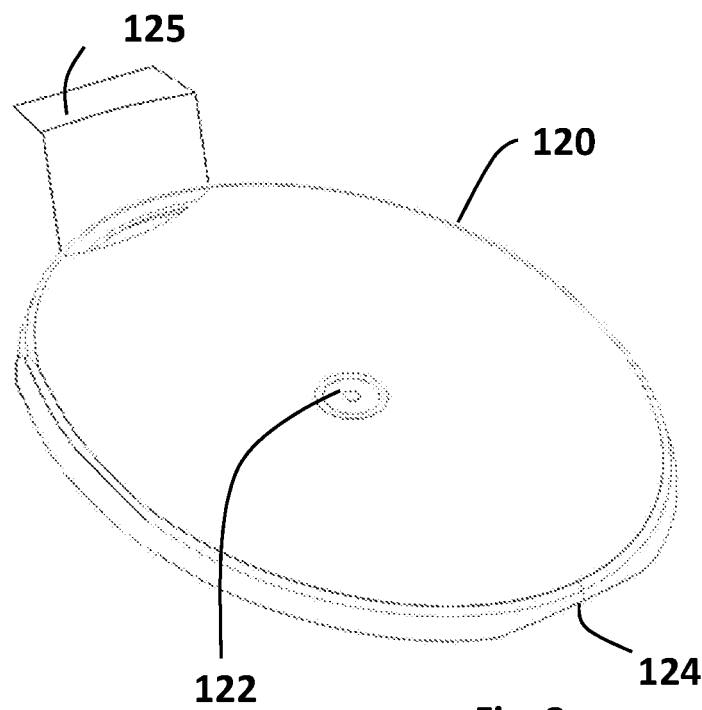
FIG. 2 shows a perspective upper view of an acoustic plate of the apparatus, according to some embodiments of the present invention.
Figure 3:
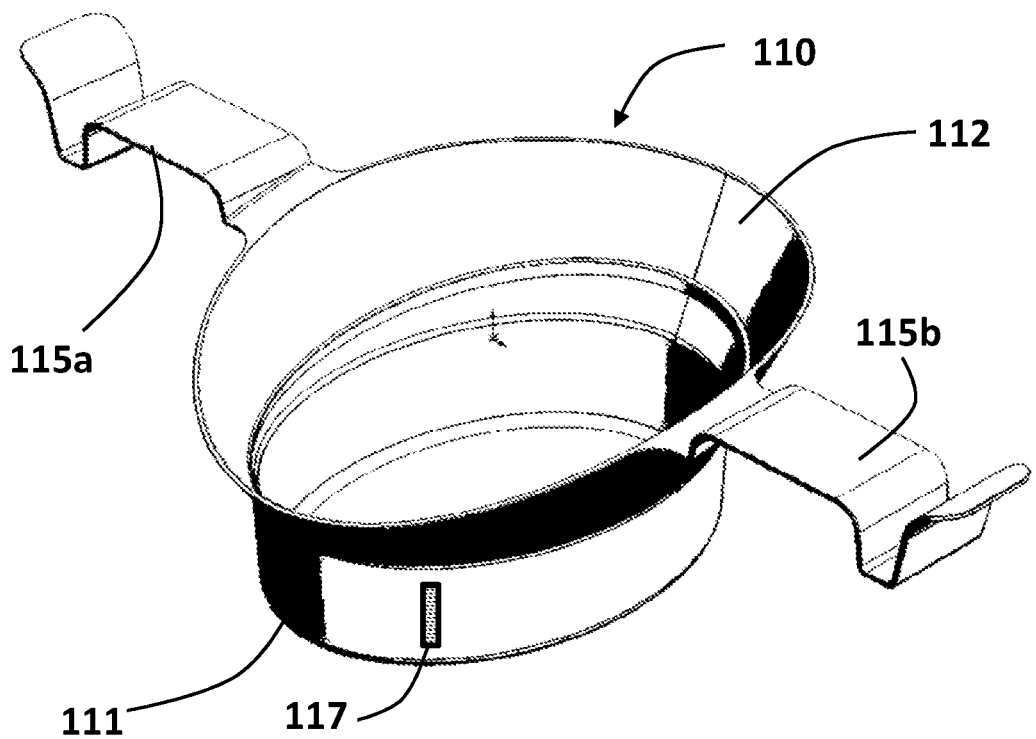
FIG. 3 shows a perspective upper view of a container of the, according to some embodiments of the present invention.

Reference is now made to FIGS. 1, 2, 3, 4A, 4B, 5A, 5B, 6A and 6B, schematically illustrating an apparatus 100 for improving acoustics for measuring quantitative urine flow rate for human male and female individuals, according to some embodiments of the invention. The apparatus 100 includes a container 110 and an acoustic plate 120. According to some embodiments, the container 110 is configured for containing liquid therein having a containing part 111 with a funnel shaped open part 112 that widens upwardly, as shown in FIGS. 1 and 3 and two hangers 115a and 115b for hanging the container 110 over the toilet bowl or toilet seat as shown in FIGS. 4A-6B. The hangers 115a and 115b can also be used for removing the container 110 from the toilet bowl 200 when urination is completed preventing contact of the individual with the container 110 for hygienic purposes.

Optionally, the container 110 also includes an indicator 117 with a scale ruler which allows an individual to view or measure the volume of urine collected inside the lower part 111 of the container 110 by, for instance being transparent allowing viewing the level of urine thereover, wherein the scaled ruler allows reading the volume associated with the level of the urine liquid.

Figure 4A:
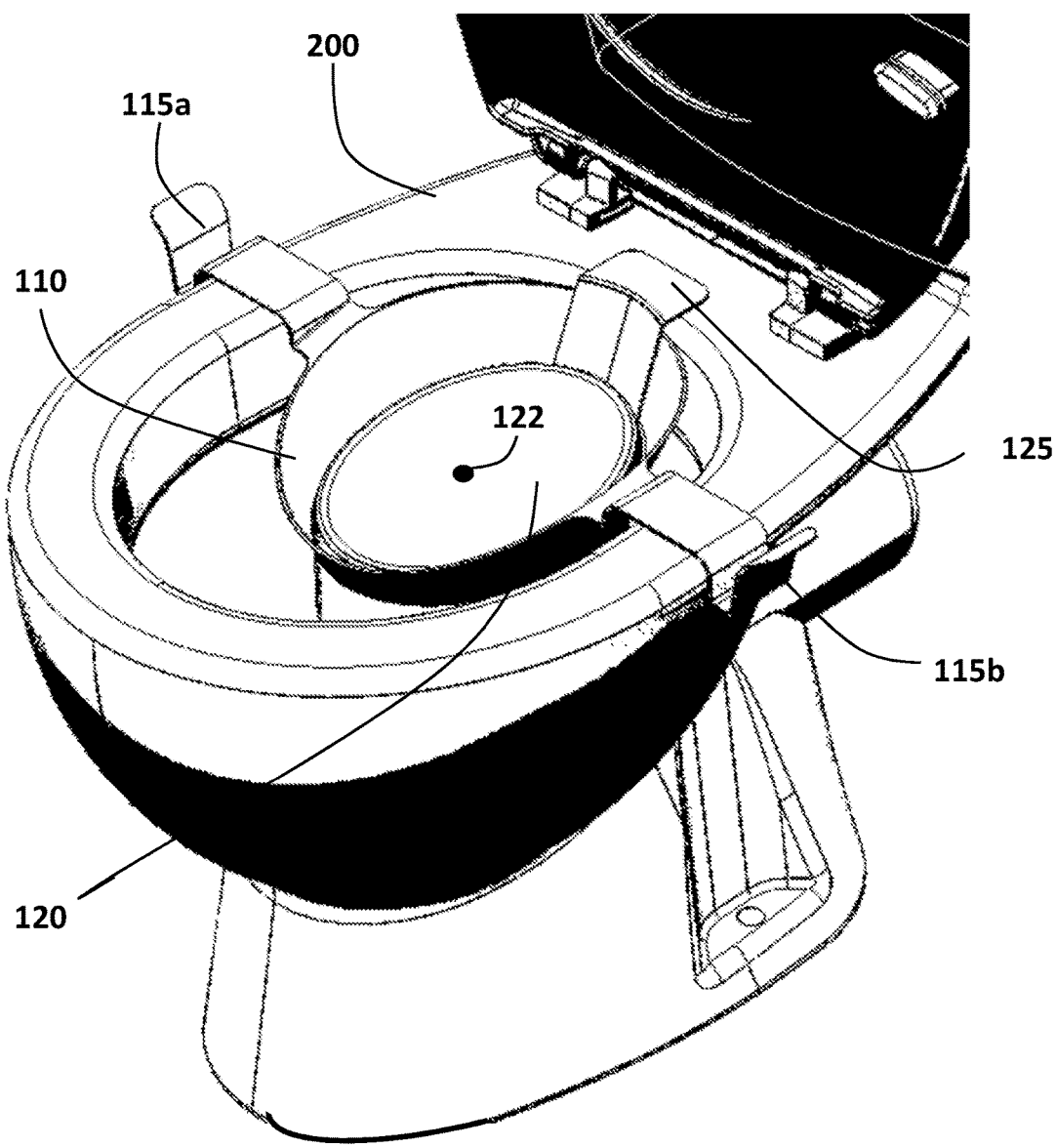
FIGS. 4A and 4B show the apparatus placed over a toilet bowl.
Figure 5A:
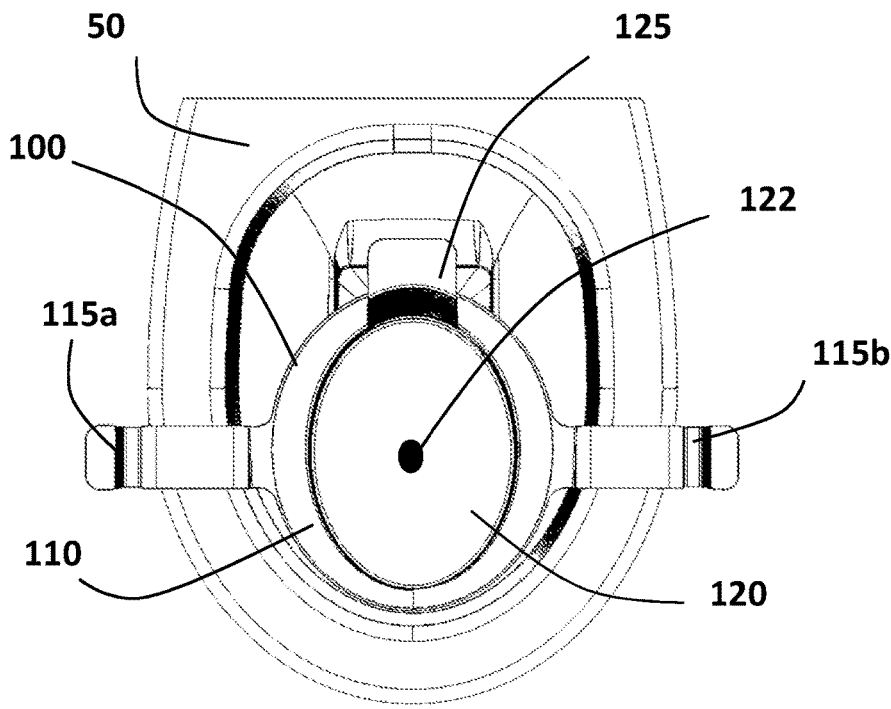
FIGS. 5A and 5B show the apparatus placed over a toilet bowl in a position that is suitable for male subjects.
Figure 5B:
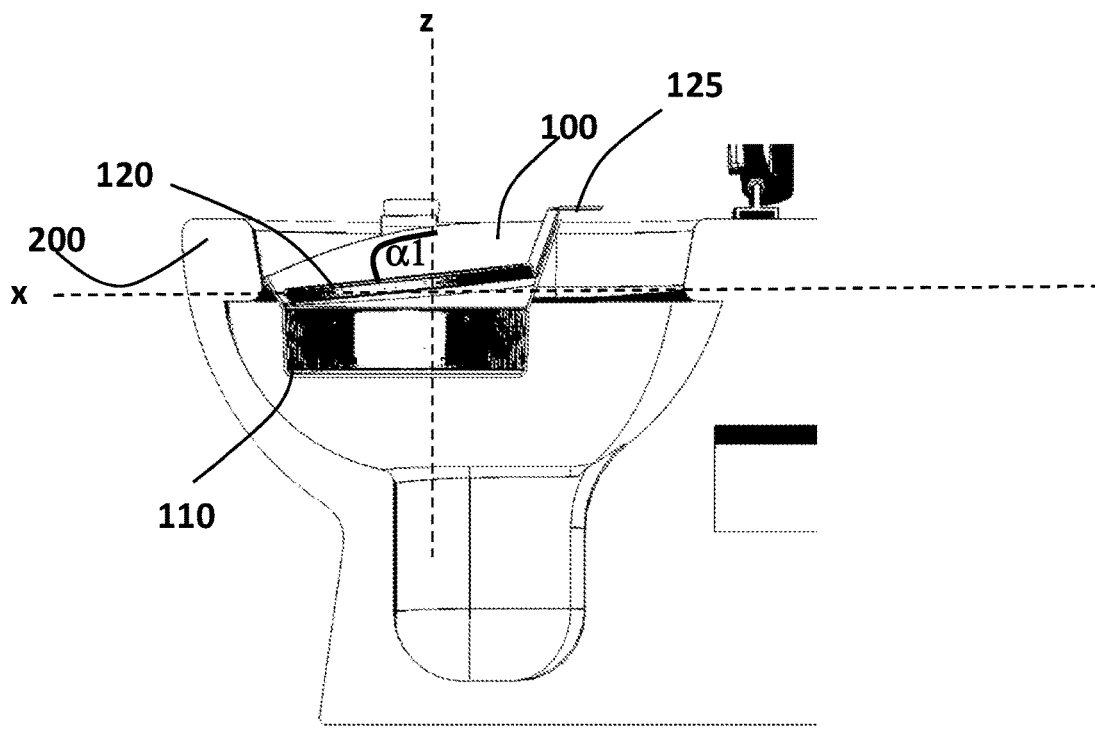
Figure 6A:
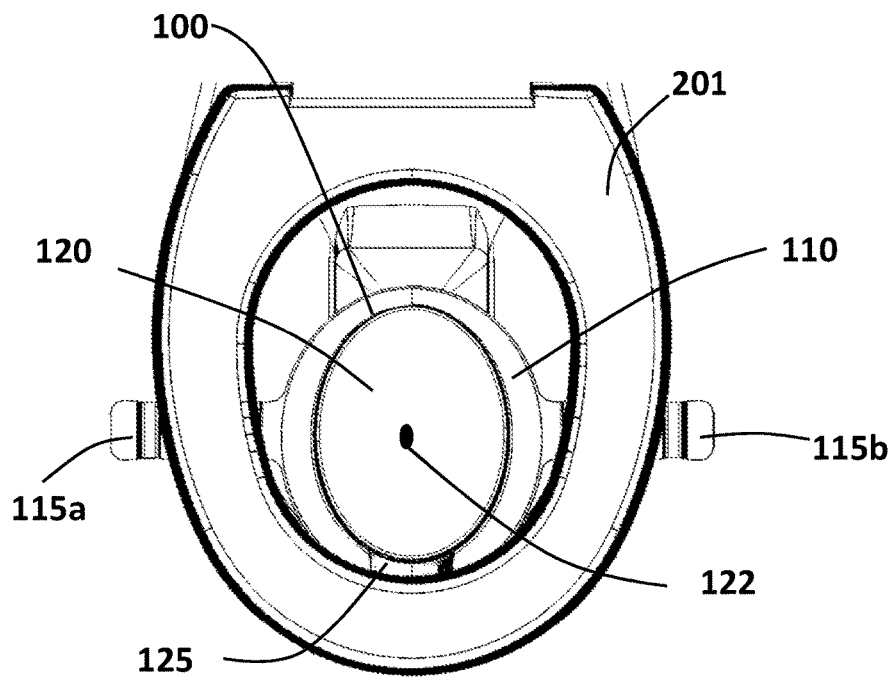
FIGS. 6A and 6B show the apparatus placed over a toilet bowl in a position that is suitable for female subjects.
Figure 6B:
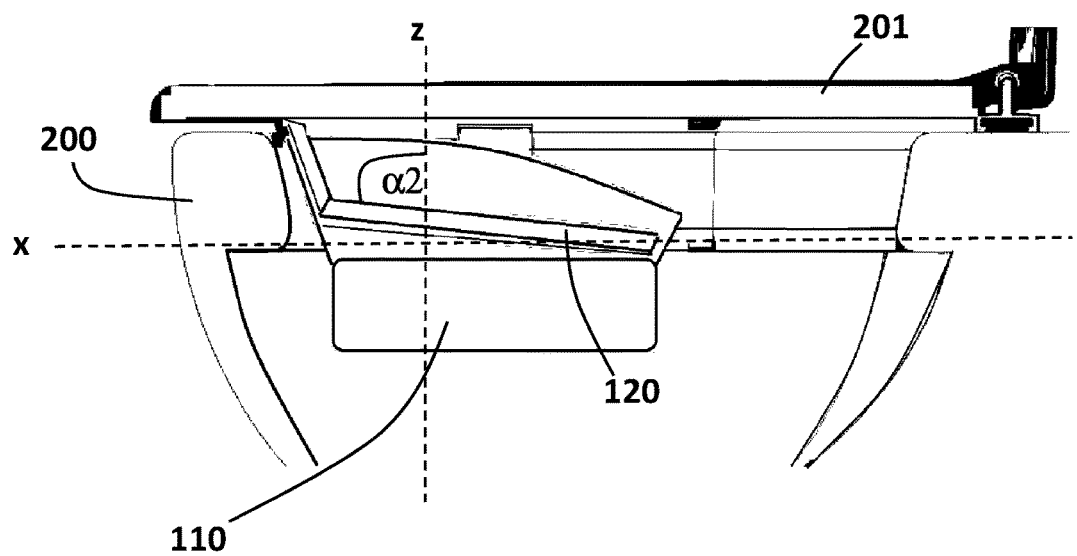

According to some embodiments, as shown in FIGS. 1, 2 and 4A-6B, the acoustic plate 120 may be an acoustic membrane e.g. made of aluminum foil and may integrally connect to a holder 125 for hanging thereof over the toilet bowl such as shown in FIGS. 4A and 6B. The holder 125 also serves for removing the plate 120 from the container 110 when urination is completed preventing contact of the individual with the plate 120 for hygienic purposes.

According to some embodiments, as shown in FIGS. 1, 2 and 4A, 5A and 6A, the acoustic plate 120 has a marking 122 indicating the center thereof or the best position thereover to point the urine flow towards for assisting the individual (especially male individuals) in directing the urine flow for optimizing acoustic measurements of the sound the urine flow will produce.

According to some embodiments, as shown in FIG. 2, the acoustic plate 120 has a truncated portion 124 configured for allowing the urine falling over the plate 120 to be collected in the container 110 there-below. The plate 120 may also be tilted forming a slope between the plate 120 and the bottom of the container 110 (where the bottom of the container 110 is substantially perpendicular to the direction of gravitation when the apparatus is placed over the toilet bowl). The slope allows directing the urine fluid from the plate 120 into the container 110 through the opening formed by the truncated part 124 of the plate 120 to optimize acoustics quality for sound measuring of the urine flow by preventing urine from accumulating over the plate 120 during urination. In this way the urine impacting the plate 120 will produce the clearest sound through the acoustic plate's membrane without or with minimum splashing of urine during urination thereover.

According to some embodiments, the apparatus 100 is designed such that it requires different positioning thereof over the toilet bowl 200 for male and female for maximum comfort and minimum splashing of the urine during each urination session.

FIGS. 4A and 5A-5B show how the apparatus 100 should be placed over the toilet bowl edge 200 for male individuals: the apparatus 100 is located at the back side of the toilet bowl 200, where the hangers 115a and 115b are hung over the bowl edge and hold the container in the bowl 200, wherein the holder 125 also hangs over the back side of the toilet bowl edge 200.

Figure 4B:
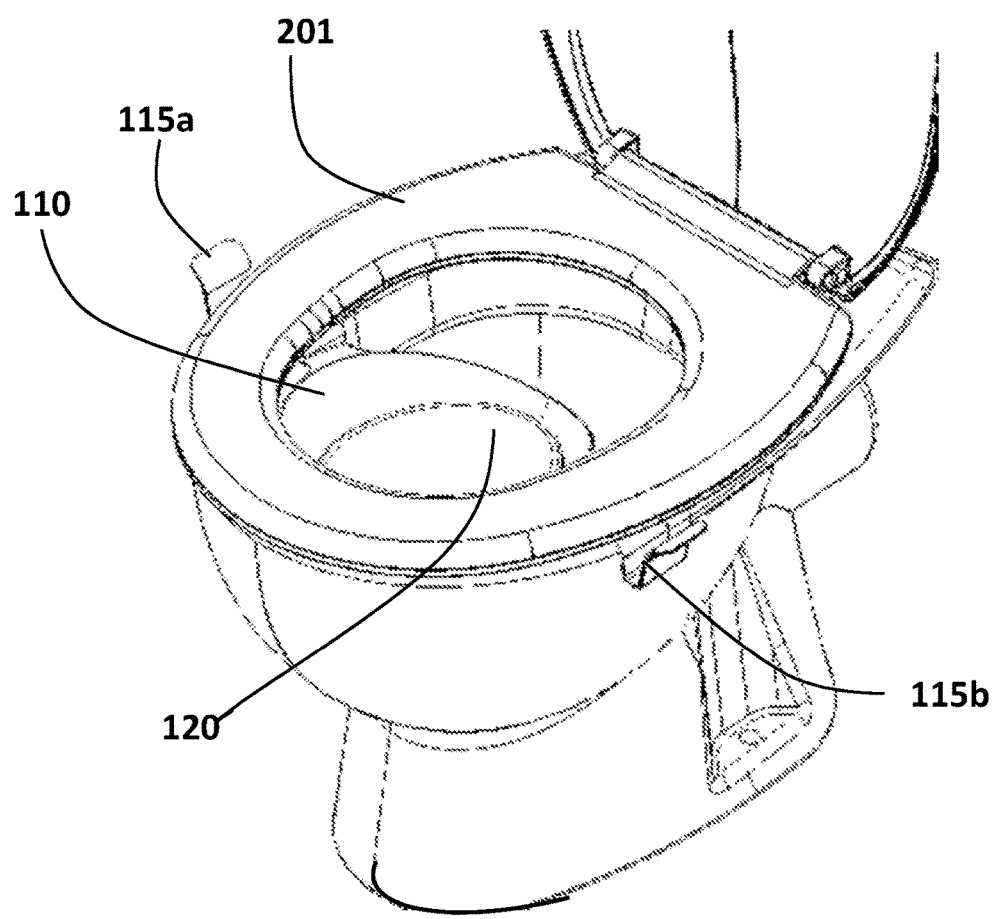

FIGS. 4B and 6A-6B show how the apparatus 100 should be placed over the toilet bowl edge 200 for female individuals: the apparatus 100 is located at a frontal end of the toilet bowl 200 hanging thereover via the hangers 115a and 115b, where the toilet seat 201 can be placed over the hangers 115a and 115b.

FIGS. 5B and 6B show how the acoustic plate 120 is tilted in respect to the bottom surface of the container 100, wherein the bottom surface of the container 110 is parallel to axis "x" perpendicular to axis "z", which indicates the gravitational direction. When the apparatus 100 is positioned over the toilet bowl 200 for male individuals, as indicated in FIG. 5B, a non-zero angle "α1" is formed between axis "z" and the sloped plate 120 wherein the plate 120 is tilted by the holder 125 thereof such that its higher end is closer to the back of the toilet bowl 200. When the apparatus 100 is positioned over the toilet bowl 200 for female individuals, as indicated in FIG. 6B, a non-zero angle "α2" is formed between axis "z" and the sloped plate 120 wherein the plate 120 is tilted by the holder 125 thereof such that its higher end is closer to the front of the toilet bowl 200.

Figure 7:
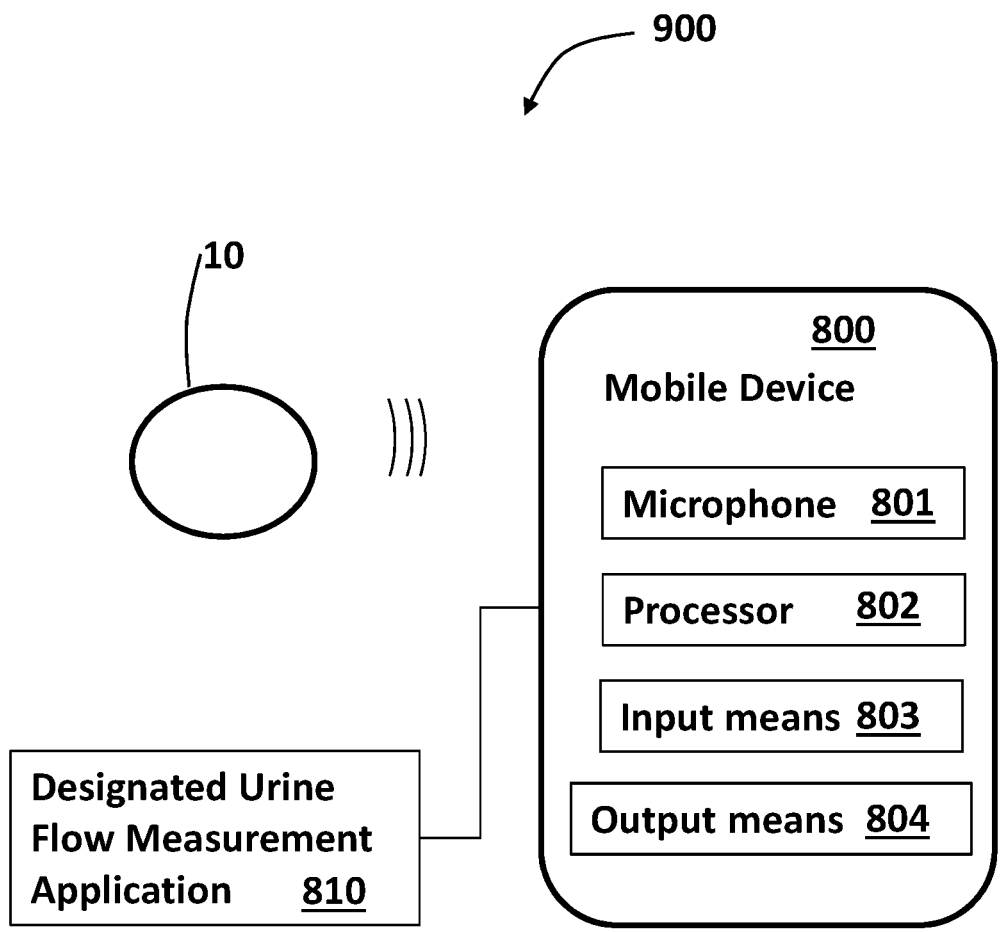
FIG. 7 schematically shows a system for measuring urine flow rate using an application operable via a mobile device, according to some embodiments of the invention.

Reference is now made to FIG. 7, showing a system 900 for measuring urine flow of a individual, according to some embodiments of the invention. The system 900 includes an apparatus such as apparatus 100 and a designated software application 810 operable through the individual's mobile device 800 that is configured for recording the sound of urine flow through a urination session of the individual, using sound detection means of the mobile device 800 such as a device's microphone 801 and analyzing the recorded sound data for calculating and outputting urine flow rate over time referred to as "Uroflow" of the specific urination session. The Uroflow can be used for analyzing the urinary condition of the individual and can be indicative of various potential related diagnoses such as male benign prostatic hypertrophy (BPH); urethral stricture disease; female incontinence; voiding dysfunction; neurogenic bladder; non-neurogenic bladder; pediatric voiding dysfunction; and pre or post bladder, prosthetic or urethral surgery condition. The individual can use the application 810 to record and analyze multiple urination sessions for follow up purposes, which may help in better diagnosing the individual's condition.

According to some embodiments, the application is configured for adapting its calculation and measures to the type of apparatus being used by having an interface allowing individuals to select the apparatus type at use. In this way the same application can be used for individuals that use various types of the apparatus producing acoustic signals that are indicative of various measures.

According to some embodiments, as shown in FIG. 7, the application 810 processes the recorded sound of urine flow through the mobile device processor 802 and also uses input and output means 803-804 of the mobile device 800 for allowing the individual to input data such as information indicative of the specific individual, date etc. and also optionally the volume of the collected urine in the container of the apparatus as measured by the individual. The output means 804 allows presenting the Uroflow and/or urine volume or other information such as potential health related condition of the individual associated with his/her Uroflow or graphs indicative of the Uroflow of the particular session and/or statistical data indicative of a number of Uroflow measures.

According to some embodiments, the application 810 is further configured for storing the Uroflow data at the mobile device data storage or transmitting the data to be stored e.g. for keeping a voiding diary of the individual and optionally also further analyzed through a remote server, using communication means of the mobile device.

Transmitting the data to the patient EMR (Electronic Medical Record). Doctor email/fax/SMS.

The mobile device can be any device that is mobile and has a processor and recording means embedded therein such as a cellular phone, a Smartphone, a tablet device, a laptop device and the like. Alternatively the recording is done via a separate recorder and the data is transmitted to be analyzed by the mobile device.

The application can be installed in the mobile device and operate solely via the mobile device or be a web application that at least partially uses the mobile device's processor for processing data.

According to some embodiments, the via a designated user interface and then simply press a virtual record button to start recording the urination session before beginning to urinate and press a virtual "end" button when urination is completed, where the recorded data can then be analyzed. The application algorithms are designed to automatically identify the beginning of urination and ending thereof within the recorded session by analyzing frequencies and amplitudes of the recorded sound signal. The sound is improved due to the acoustic qualities of the apparatus and can still be further noise-reduced and cleared for the calculation of the flow rate over time.

The system 800 allows easy and private self-measuring of urine flow rate providing the individual with a user friendly apparatus and application that can help the individual at least in recording the urine flow sound and analyzing thereof for producing the Uroflow output. The outputted Uroflow of each session or of several urination sessions of the individual can then be professionally interpreted by one or more professionals to assist in the diagnostic of the individual.

According to some embodiments, the application also receives and stores user input indicative of the volume of the collected urine read by the individual through the indicator over the apparatus or measured by the individual in any other way. Alternatively or additionally, the volume of urine is automatically calculated from the urine volume measurement.

According to other embodiments, the urination sound and/or vibrations is/are sensed via s a transducer sensor (e.g. piezoelectric transducer) located at the apparatus, where the apparatus further includes transmission means for transmitting signals indicative of the recorded signals via a communication link to the mobile device for processing thereof. The communication link may be wireless of a communication cable transmitting electric or optical signals.

Figure 8:
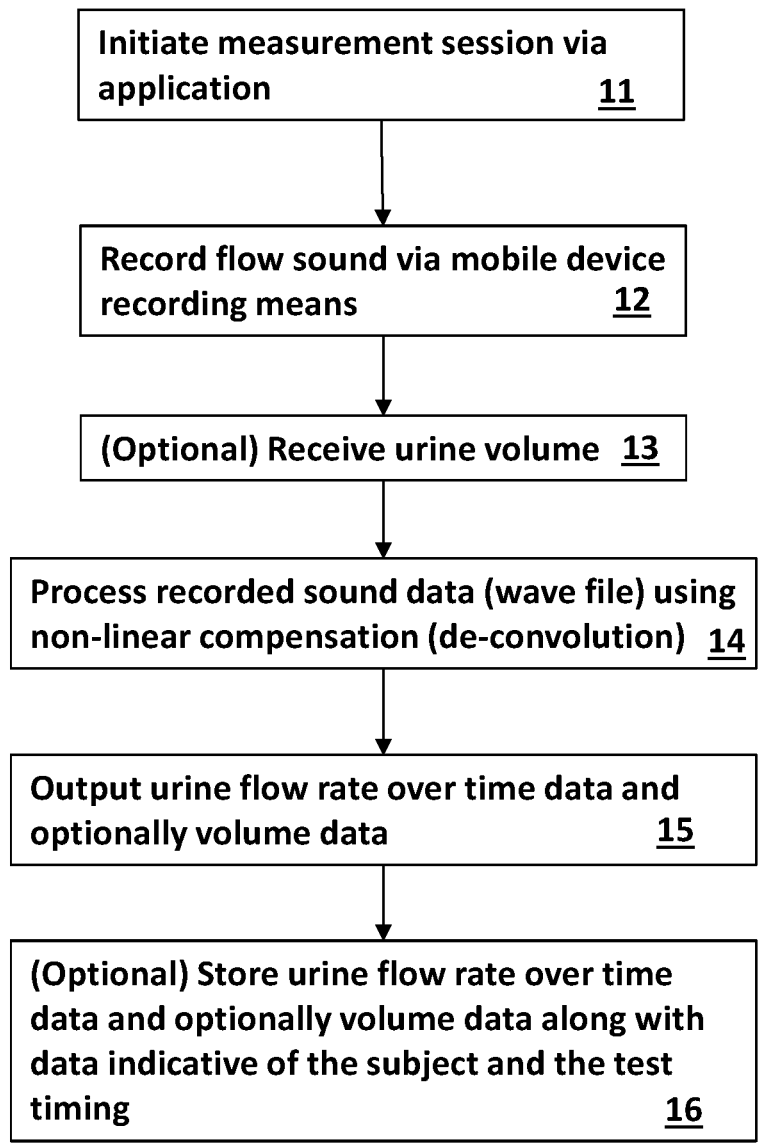
FIG. 8 is a flowchart schematically showing a process of measuring urine flow rate using the application operable via the mobile device, according to some embodiments of the invention.

Reference is now made to FIG. 8, which is a flowchart schematically showing a process for measuring urine flow rate, according to some embodiments of the invention. A preliminary step of placing of the apparatus over the toilet bowl may be required before the measuring process begins. The individual uses the designated application through his/her mobile device to initiate a measurement session 11 e.g. by entering the application and pressing a "go" button. Once the measurement session is initiated, the application begins recording sound around the mobile device until the individual stops the recording 12. Optionally, the volume of the collected urine is inputted by the individual and received and stored by the application 13. The recorded sound data is then processed via the application to calculate the Uroflow by using, inter alia, a non-linear compensation process (deconvolution), which will be further explained below 14. The Uroflow is then outputted 15 and/or stored 16.

Figure 9:
FIG. 9 shows an interface screen with a "Go" button allowing initiating the recording of urination sound as one of the screens of the application.

FIG. 9 shows an example of a user interface screen allowing the individual to press a virtual "Go" button to begin the recording.

Figure 10:
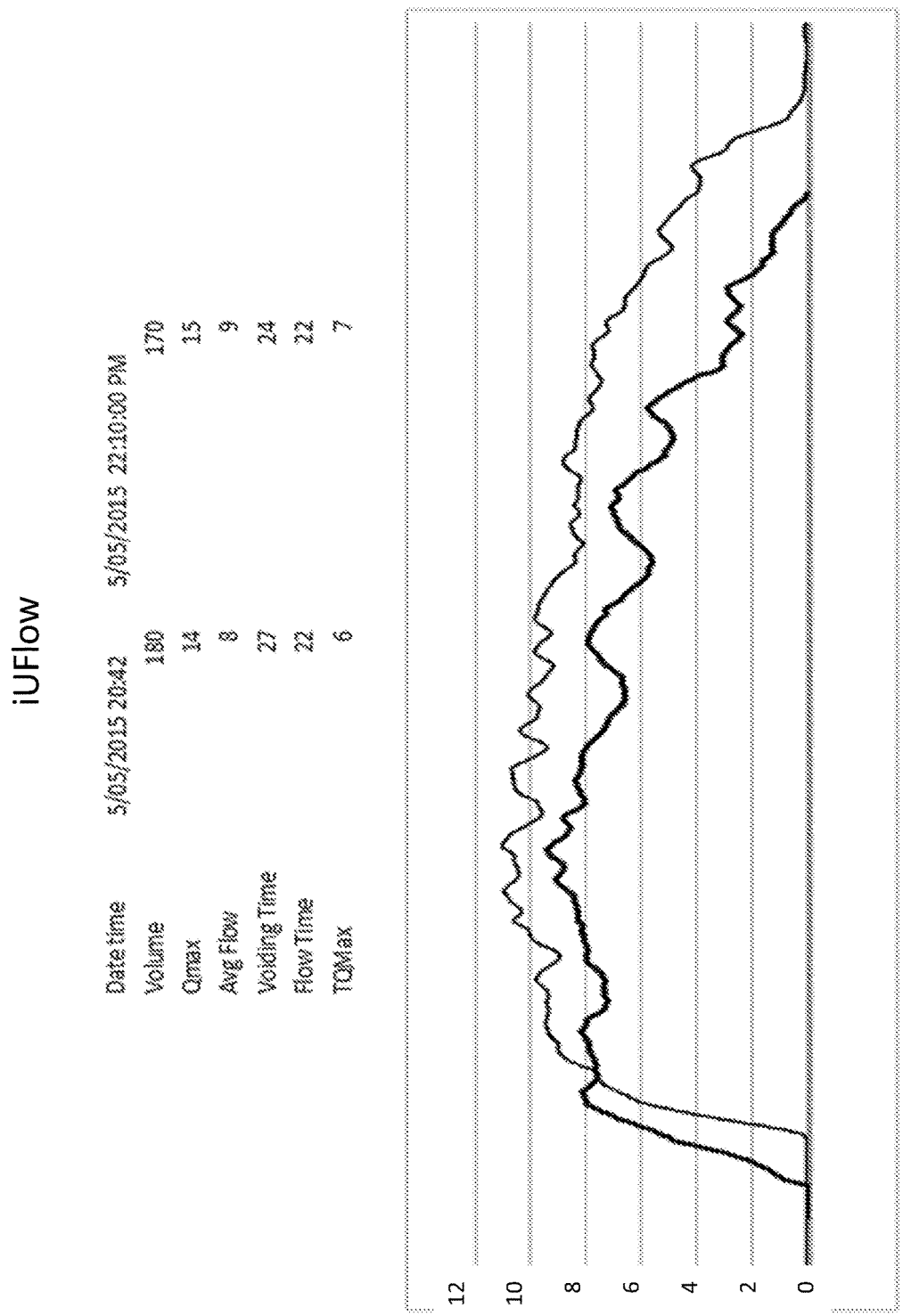
FIG. 10 shows a screen presenting an output Uroflow diary showing a histogram of flow rate vs. time.

FIG. 10 shows a screen presenting an output Uroflow diary showing a histogram of flow rate vs. time.

FIG. 11 shows another Uroflow output table indicative of follow up on volume of urine samples for different measurement sessions.

Figure 12A:
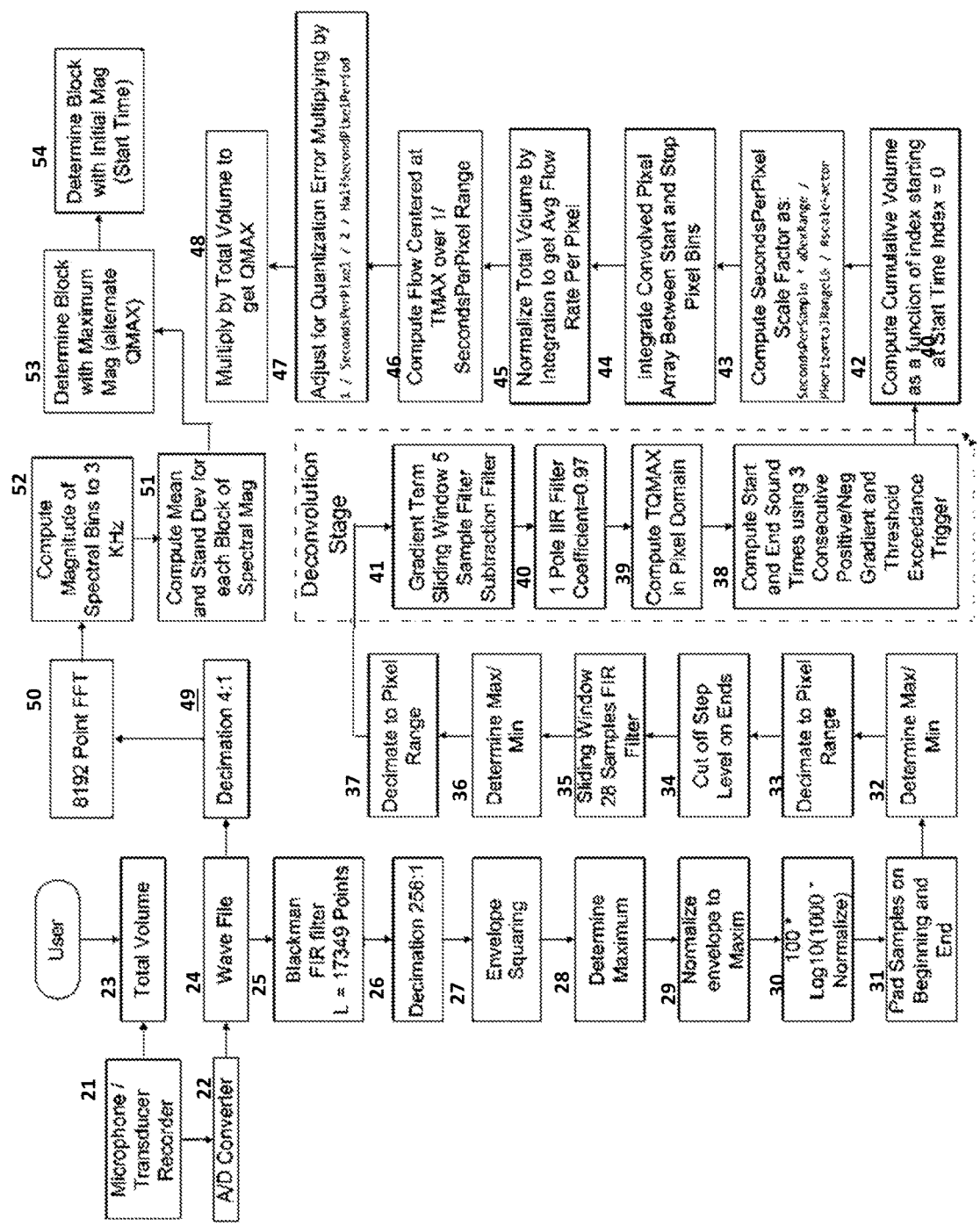
FIGS. 12A and 12B show flowcharts of processes for processing the recorded urination sound signals (sound data), according to one embodiment of the invention.
Figure 12B:
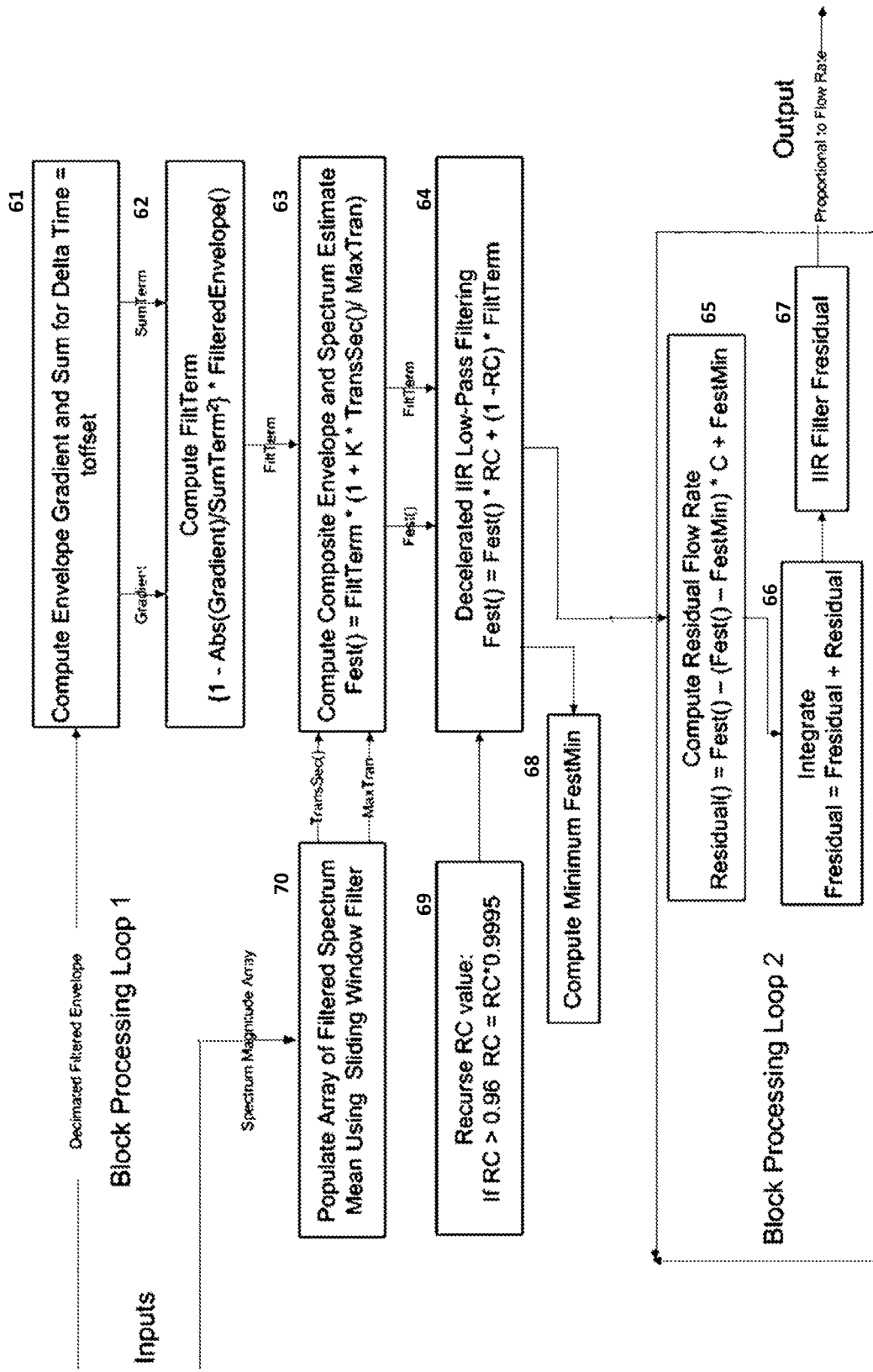

Reference is now made to FIGS. 12A and 12B showing flowcharts of processes for processing the recorded urination sound signals (sound data), according to one embodiment of the invention. In FIG. 12A, steps 21-37 show how the signal of the sound data is processed to determine end and beginning of actual urination and for noise reduction and signal spectral envelope filtering. Steps 36-41 show how the sound data outputted from the spectral enveloping process is further processed by using non-linear compensation (de-convolution). Steps 42-53 show how the Uroflow is finally calculated. FIG. 12B shows a flowchart of steps 61-70 for the non-linear compensation process.

According to this embodiment, the processing of the recorded sound data roughly includes:
1. Spectral envelope filtering.
2. Decimation and low-pass filtering of the time domain signal.
3. Log based scaling of the envelope.
4. Additional low-pass filtering.
5. De-convolution to achieve an approximate linear relationship to the actual flow rate.

According to this embodiment, to achieve a quantitative measurement of the urine flow the total volume of the collected urine is required as an input. The objective is to achieve an output time profile proportional to an actual flow rate measurement reference permitting quantitative based flow rate estimates valid over 1 second intervals.

The defined "de-convolution" fifth stage incorporates two forms of de-convolution in addition to selective processing techniques. The approach is based on several hypotheses, namely:
1. Log-based envelope processing of the audio is a first-order approximation to linear flow rate.
2. Accuracy of the envelope processing is enhanced through the use of a combination of the time domain and spectral mean values. Spectral processing (quadrature correlation) has shown a natural ability to attenuate the impact of un-correlated and many artifact noise samples.
3. One element of physical phenomena related excessive cumulative flow volume is measured and compensated. This method is a form of de-convolution followed by regeneration. The time domain flow rate from a mechanical flow reference produces a "Urofile" (Uroflow data file) result for analysis purposes. The profile of the Urofile is emulated in part through residual subtraction of "excess" flow volume. An improvement in the model predicts excess volume to occur at certain points of time based on the flow rate exceeding the saturation point to the exclusion of scalable flow rates versus time. During the urine collection and recording process the accuracy of the instantaneous value of the flow rate is highest when the localized volume on the plate is close to zero. The model assumes this doesn't always happen (although the urine is directed by the plate slope into the container of the apparatus), causing a residual volume on the plate to be greater than zero when the input flow rate is sufficiently high. The threshold in the flow rate that is used to determine when it occurs is modeled as a high fraction, e.g., 0.9 times the maximum flow rate whereby the net accumulation or residual exceeds zero. Similarly a depletion of the residual, if measurable, occurs when the flow rate is less than the threshold (or equilibrium point). Therefore a subtraction is implemented. This is a computation of fluid latency caused by the dispersed portions of the urine flow of high speed columniation and splashing of urine. The model asserts that this latency is proportional to the rate of change of the flow magnitude which is the temporal gradient of the envelope magnitude. A small fraction of this magnitude change or gradient is subtracted from the normalized filtered magnitude.
4. A second element of over-compensation has been implemented to account for gravity induced delays in the flow rate. Height differences in columns and plate slope affect propagation time of water droplets. Given other effects including surface tension is hypothesized that the delay is proportional to the time gradient derived from the sound profile. This smearing of time or dispersion is compensated by a gradient subtraction technique.
5. Recursive modification of the time-constant used during low-pass filtering is accentuated during the early sample values of this processing stage. Initially the time constant starts very high at 10 thousand and diminishes approximately to 20 within a small fraction of the analysis period. The original recursive coefficient used for filtering begins at 0.9995 but does not remain constant as in standard filters. it is diminished over time using a second stage process. The time constant in general is approximately the 1/(1-RC). The reduction of RC is also handled iteratively using a factor of 0.9999 consequently the RC factor diminishes after each sample until it reaches a terminal limit. In other words, for example, RC=0.9999*RC after each sample. Therefore the time constant gets smaller. When RC is high the filtering is high and commensurately the time constant is high.

Any other methodology can be used for processing the recorded sound data for calculating the flow rate vs. time data of urination sessions and any other method for signal noise-reduction and compensation can be used to allow optimizing the accuracy of the flow rate calculation algorithm.

Figure 13:
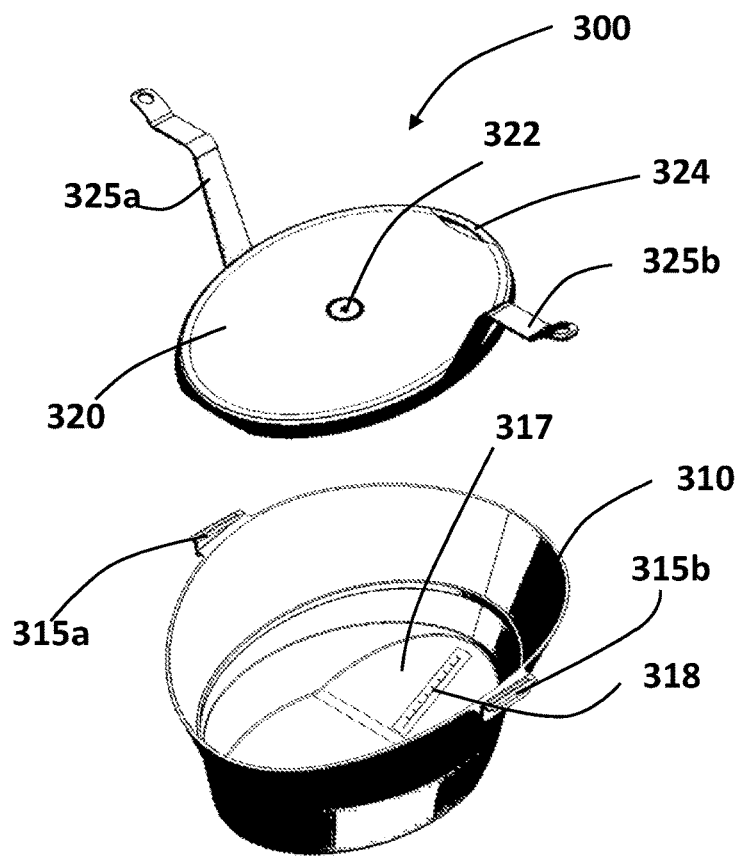
FIG. 13 shows an exploded view of an apparatus for collecting urine and for improving acoustics of urination sound for urine flow and volume measuring, according to other embodiments of the invention.
Figure 14:
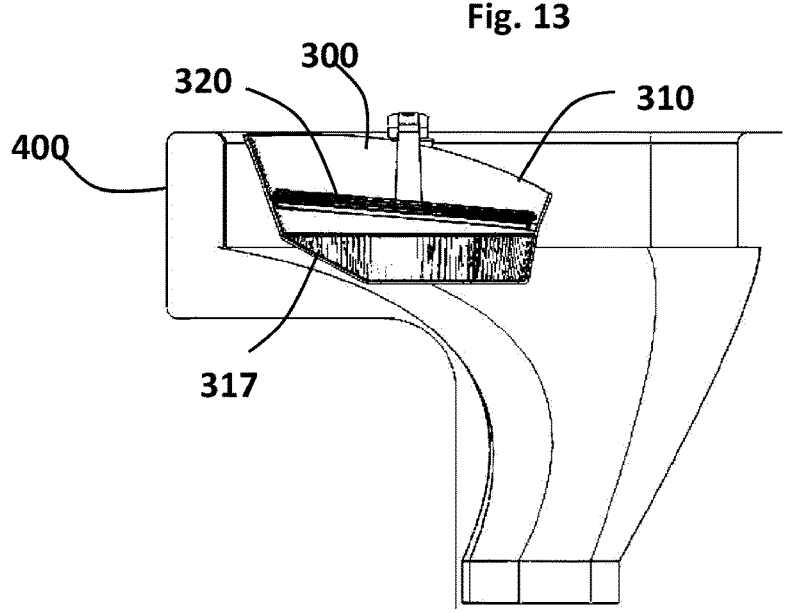
FIG. 14 shows a transparent side view of the apparatus of FIG. 13, according to the other embodiments of the invention.

Reference is now made to FIGS. 13 and 14 showing an apparatus 300 for collecting urine and for improving acoustics of urination sound, according to other embodiments of the invention. This apparatus 300 includes an acoustic plate 320 having an acoustic membrane such as an aluminum foil and a container 310. The acoustic plate 320 is placed over the container 310 such as to form a space between a bottom of the container 310 and the plate 320 surface to allow urine to accumulate under the plate 320. The plate 320 is also tilted in respect to the bottom of the container such as to direct urine flow into the container 310 when the apparatus 300 is used and placed over the toilet bowl 400. This configuration prevents urine from accumulating over the plate's surface during urination and therefor improves acoustics of the sound made by the urine flow thereover.

As illustrated in FIG. 13, the acoustic plate 320 also has a marking 322 for indicating the best position over the plate to which the individual is to direct his urine flow and a truncated portion 324 for forming an opening that will allow the urine to flow into the container 310. The acoustic plate 320 also has handles 325a and 325b for placing the plate 320 over the container 310 and for maintaining the plate 320 over the container 310 such as to form the space between the tilted plate 320 and the bottom of the container 310. The handles 325a and 325b also allow the individual to remove the plate 320 from the container 310 without touching the plate area. The container 310 includes hangers 315a and 315b for allowing the individual to hold the container 310 for placing it over the toilet bowl and removing it therefrom and also for hanging the apparatus 300 over the toilet bowl 400 edge as shown in FIG. 14.

According to some embodiments, as shown in FIG. 14, the bottom of the container 310 has a tilted part 317 with an indicator 318 ruler for allowing the individual to measure the volume of the accumulated urine in the container 310.

The container may be made from any known in the art material such as plastic, formable plastic sheet, polystyrene, acrylic aluminum and the like.

Figure 15:
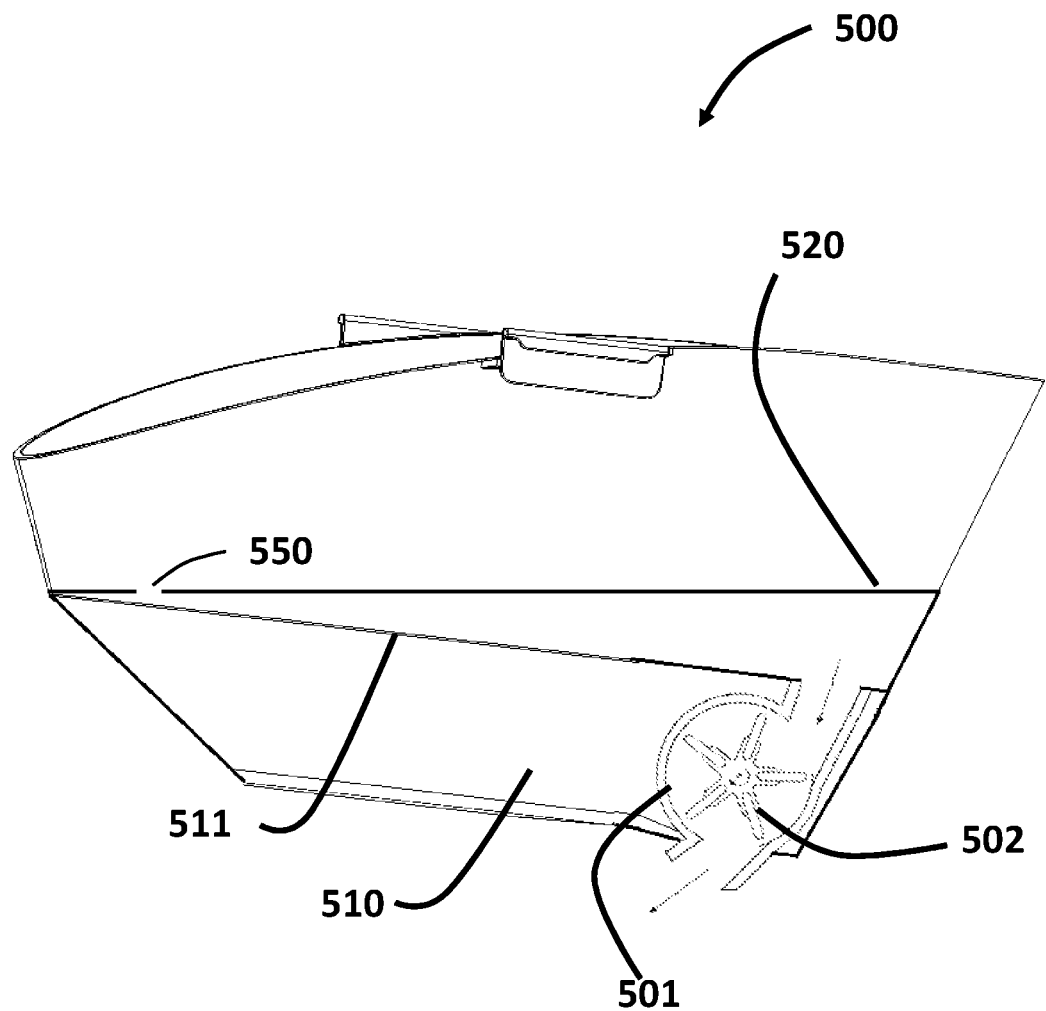
FIG. 15 shows a side view of an apparatus for measuring urine volume using a paddlewheel sensing device, according to other embodiments of the invention, having a mechanical fluid volume sensor.
Figure 16A:
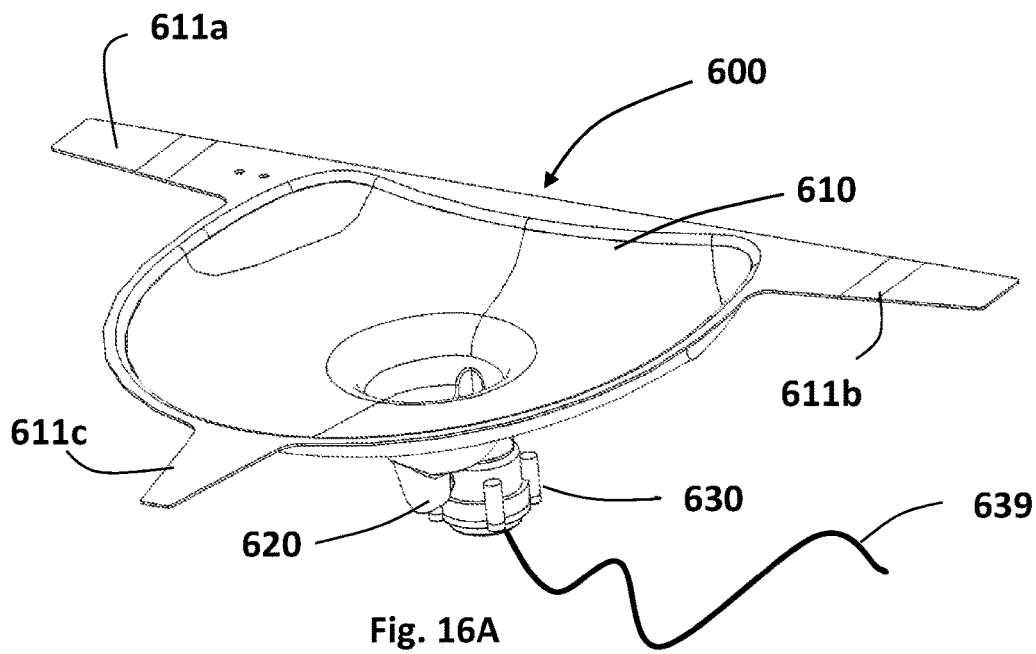
FIGS. 16A and 16B show an apparatus for measuring urine volume using a paddlewheel sensing device, according to other embodiments of the invention.
Figure 16B:
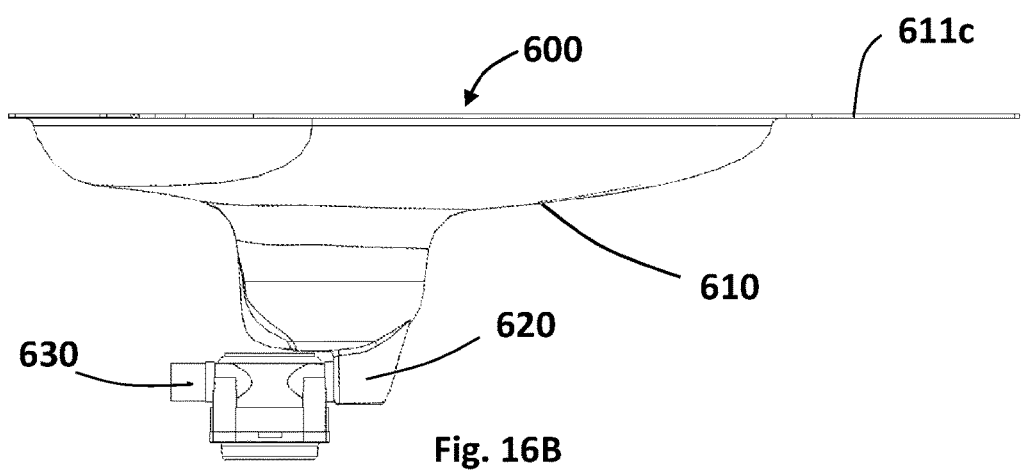

Reference is now made to FIG. 15, which shows an apparatus 500 for measuring urine volume having a paddlewheel sensing device 501, according to other embodiments of the invention. The apparatus 500 also includes a container device 510 and an acoustic plate 520 placed in the container such that it forms a slope to direct urine towards the bottom of the container 510. In this particular design, the acoustic plate 520 directs the urine to another plate 511 of the container device 510 via opening 550 further directing the urine liquid to another edge thereof for directing the urine into the paddlewheel sensing device 501.

The paddlewheel sensing device 501 allows automatic measuring of the volume of urine inside the container device 510 by having the directed urine liquid rotate a turbine wheel 502 thereof. The wheel 502 either connects to a sound mechanism that produces a distinguishable indication sound after each individual paddle and/or full rotation of the wheel 502 or produces electromagnetic signals upon rotation using magnets for instance (designed as an Hall effect sensor). Each individual paddle and/or a full rotation of the wheel 502 is indicative of a known liquid volume portion. This distinguishable sound (e.g. caused by using a bell or a piece vibrated by the turning of the wheel 502) is detectable and recognizable by the software application and can be recorded or simply detected in real time by the device's microphone along with urination sound. The application will automatically calculate the overall volume of the urine throughout the urination session by counting the number of times the distinguishable sound was produced by the paddlewheel sensing device 501. The rate of the distinguishable sound (the number of times the wheel made a distinguishable sound per time unit) can also be used to calculate or improve calculations of the urine flow rate and/or changes thereof during that same urination session by the application.

Figure 17:
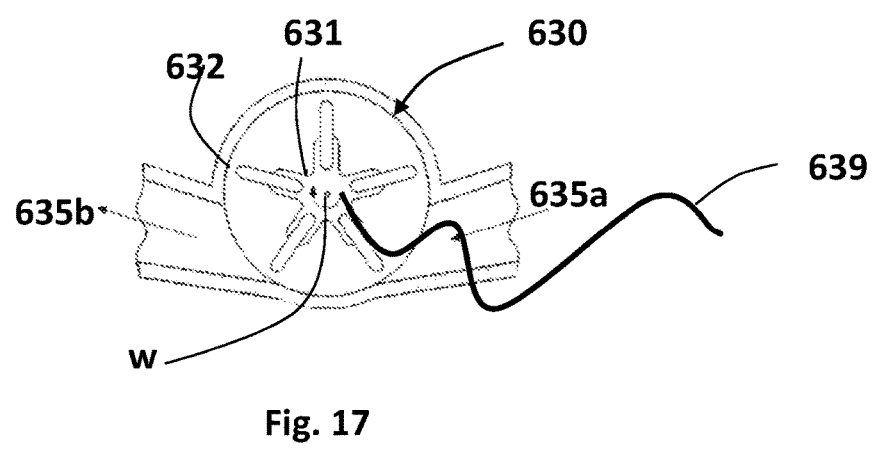
FIG. 17 shows the paddlewheel sensing device of the embodiments portrayed in FIGS. 16A-16B.
Figure 18:
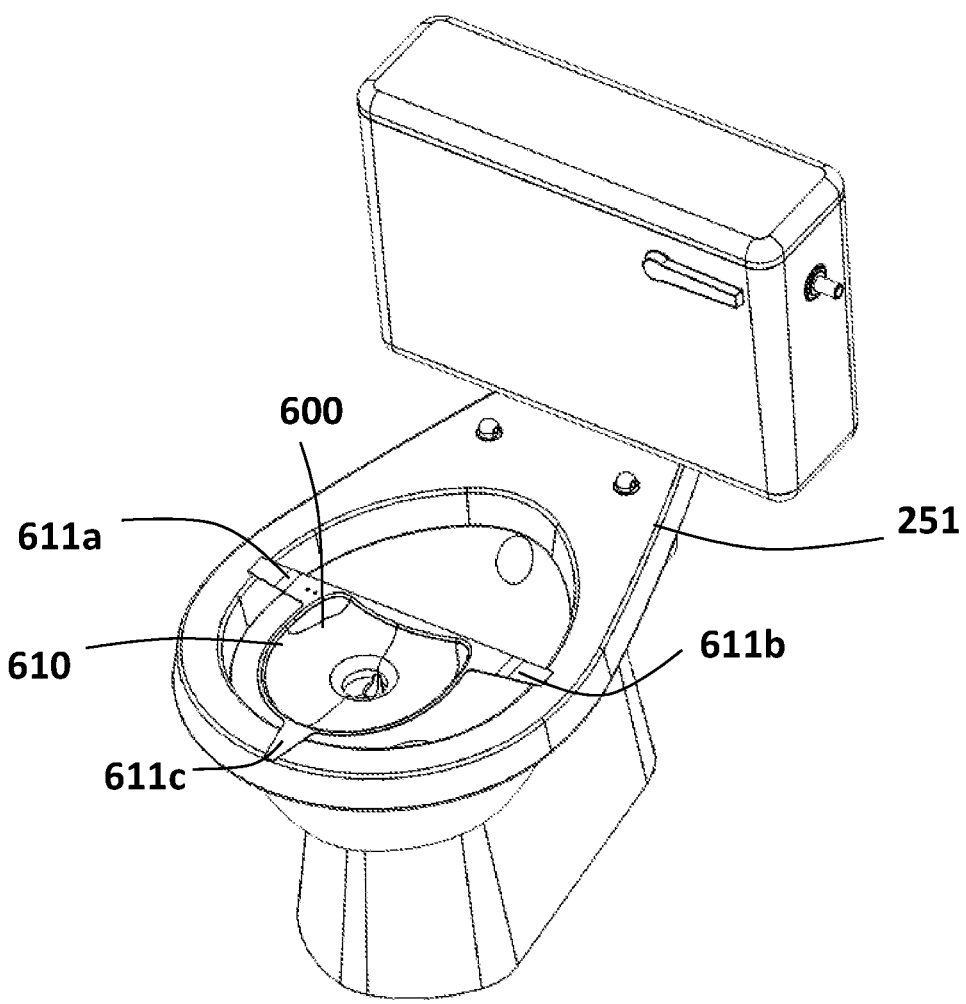
FIG. 18 shows the apparatus of FIGS. 16A-16B placed over a toilet bowl in an elevated perspective view.

FIGS. 16A, 16B, 17 and 18 show an apparatus 600 for measuring urine volume using a paddlewheel sensing device 630 or part thereof, according to other embodiments of the invention. The apparatus 600 in this case includes a bowl or funnel shaped body 610 having holders 611a-611c configured for hanging the apparatus 600 over the toilet bowl or seat; a directing conduit 620 for directing the urine therethrough; and the paddlewheel mechanical volume sensing device 630. The bowl shaped design of the body 610 and the conduit 620 extending from its bottom opening direct the urine through the entrance 635a of the sensing device 630 for rotating the wheel 631 thereof over its axis "w". The sensing device 630 also includes sound producing means (not shown) which produce indication sound upon each full spin of the wheel 631 or partial spin thereof. As illustrated in FIG. 17, the wheel 631 includes multiple blades for being rotated upon receiving urine liquid flow thereover. The sensing device 630 housing 632 is designed such that it includes an entrance 365a tube like inlet and an exit 635b tube like outlet. FIG. 18 shows how the apparatus 600 can be placed over a toilet bowl 251.

According to some embodiments of the invention, the paddlewheel sensing device 630 uses an Hall effect for generating a pulse upon predefined full or partial spin comprising magnets therein rotatable by the paddlewheel blades 631 such that when the blades of the wheel 631 spin they generate a magnetic force transformed into an electric signal (electric pulse) that may be used for generating current that can be directed to the end device via a connecting cable 639 such as a headphone jack which can convert in turn the incoming electric signal into audio signal, or for producing RF (radio frequency) based signals (indicative of the volume portion sensed thereby) transmittable to the user's end device for reading thereof. Alternatively, the current produced is used for operating a circuitry that can switch on a sound effect (not shown) for producing a distinguished sound recognizable by the application for acoustic identification of volume.

Figure 19:
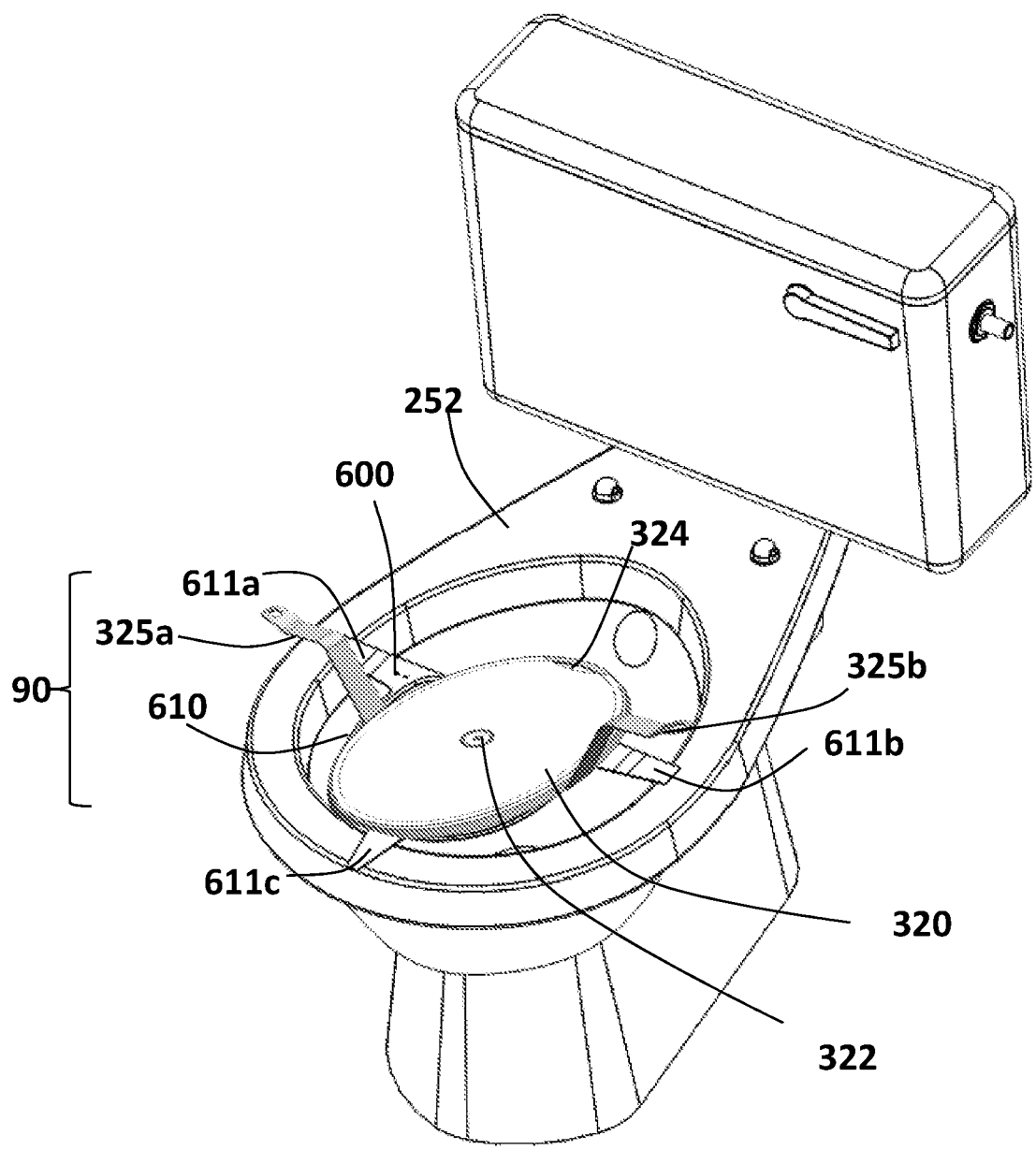
FIG. 19 shows a combined apparatus for measuring urine flow and volume, according to some embodiments of the invention, comprising both the apparatus portrayed in FIGS. 16A and 16B which includes the paddlewheel sensing device for direct urine volume measuring and the acoustic plate as portrayed in FIG. 13 for improving urination acoustics.

FIG. 19 shows a combined apparatus 90 for measuring urine flow and volume placed over a toilet bowl 252, according to some embodiments of the invention. The combined apparatus 90 includes the apparatus 600 according to embodiment portrayed in FIGS. 16A and 16B which includes the paddlewheel sensing device 630 for direct urine volume measuring and the acoustic plate 320 as portrayed in FIG. 13 for improving urination acoustics.

The assembly 90 allows the application of the system, upon receiving recorded or real time acoustic signals during an urination session of an individual, to measure both flow rate and/or flow rate behavior as well as to measure quantity of the urine. The overall acoustic signal detected by the acoustic sensing means of the end device is analyzed to distinguish sound indicative of the urine flow impacting the acoustic plate 320 from the sound produced by the paddlewheel sensing device 630 of the apparatus 600 indicative of volume of urine and optionally also indicative of urine flow rate. The two distinctable acoustic signals when separated by the application can then be used for robust estimation of the urine flow rate, urine quantity and optionally also for estimating urine flow rate behavior (changes).

According to some embodiments of the invention, the application may be configured to produce a urine measurements (voiding) diary recording the measured parameters such as urine flow rate, flow rate changes and/or urine quantity for each session and identification data of the particular session such as the date and time and individual. This diary may be helpful in diagnosis of various medical conditions of the individual and will allow the individual to monitor urine related measures thereof without having to go to the clinic for measuring or to report to the clinic. The data of the diary and updates thereof may be automatically transmitted to an end device of a clinic or a professional person for analysis of the recorded measures and/or be automatically analyzed by the same or another software module for diagnosing the individual's condition or at least for identifying alarming measurement values for transmitting alerts to the individual and/or to a clinic center or professional person for further follow-up and treatment.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments and/or by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

Although the invention has been described in detail, nevertheless changes and modifications, which do not depart from the teachings of the present invention, will be evident to those skilled in the art. Such changes and modifications are deemed to come within the purview of the present invention and the appended claims.

The invention claimed is:

1. An apparatus for determining or measuring at least one parameter related to urination of an individual, said apparatus is characterized by being configured to produce at least one of improved acoustic and electromagnetic signals indicative of said at least one urination parameter upon having urine applied thereover, said apparatus comprising an acoustic plate for improving the sound of a urine flow for improved measuring of the urine flow, said plate is configured for vibrating in response to the urine flowing thereover.

2. The apparatus according to claim 1, wherein said acoustic plate comprises an acoustic membrane.

3. The apparatus according to claim 1, wherein said acoustic plate is held in the apparatus in a tilted manner in respect to the direction of gravity to also direct the urine to flow therefrom.

4. The apparatus according to claim 1, wherein said apparatus further comprises a collecting container configured for hanging over the toilet bowl or seat, said collecting container allows collecting urine for at least one of improving acoustics of the acoustic plate and quantitative measuring-thereof.

5. The apparatus according to claim 4, wherein said container comprises an indicator for indicating a measure related to the volume of the urine therein.

6. The apparatus according to claim 1, wherein said apparatus comprises at least one holder for hanging over a toilet bowl or toilet seat.

7. The apparatus according to claim 1, comprising:
a) a body configured for hanging over a toilet seat or bowl;
b) a mechanical sensing device for mechanically measuring at least one of urine flow and urine quantity, said body being configured to direct urine therefrom into said mechanical sensing device; and
c) at least one means for producing electromagnetic signals indicative of the measured flow or quantity during a urination session,
wherein said apparatus is configured such as to mechanically produce an electromagnetic signal indicative of a known quantity of urine whenever such quantity is measured thereby.

8. The apparatus according to claim 1 comprising a transducer sensor and plate attached thereto configure for sensing urination related vibrations and transforming these vibrations into electronic signals.

9. The apparatus according to claim 1, said apparatus being configured to measure or calculate at least one of the following parameters: urination flow rate, urination volume, urination flow rate changes through time based on at least one of produced acoustic and electromagnetic signals depending on the type and configuration of the apparatus being used.

10. An apparatus of claim 1, wherein the determining of at least one said parameter includes identifying urination flow rate behavior pattern based on at least one of produced acoustic and electromagnetic signal.

11. A system for determining or measuring at least one parameter related to urination of an individual, said system comprising:
a) an apparatus characterized by being configured to produce improved acoustic signals indicative of said at least one urination measure upon having urine applied thereover, said apparatus comprising an acoustic plate for improving the sound of a urine flow for improved measuring of the urine flow, said plate is configured for vibrating in response to the urine flowing thereover; and
b) an application module operable via an end device, said application module being configured to detect acoustic signals originating from said apparatus and calculate said at least one measure related to at least one of urine flow and urine quantity therefrom, wherein said application is adapted to use acoustic sensing means and processing means of the end device via which it operates,
wherein the determining of at least one parameter includes identifying urination flow rate behavior based on at least one of produced acoustic and electromagnetic signals.

12. The system according to claim 11, said application module further being configured to record the acoustic signals for offline processing thereof.

13. The system according to claim 11, said application module being configured to measure or calculate at least one of the following parameters: urination flow rate, urination volume, urination flow rate changes through time based on at least one of produced acoustic and electromagnetic signals depending on the type and configuration of the apparatus being used.

14. The system according to claim 11, wherein said mechanical sensing device comprises a paddlewheel sensing device having a wheel of blades rotatable about an axis upon application of urine thereof, said bowl shaped body being configured to direct the urine to flow through said wheel, wherein said sensing device is configured such as to produce an indication electromagnetic signal upon full or partial rotation of its wheel.

15. The system according to claim 11, said application module comprises a user interface allowing individuals to define beginning and ending urination.

16. An apparatus for determining or measuring at least one parameter related to urination of an individual, said apparatus is characterized by being configured to produce at least one of improved acoustic and electromagnetic signals indicative of said at least one urination parameter upon having urine applied thereover, said apparatus comprises a mechanical sensing device, said mechanical sensing device comprises a paddlewheel sensor based on Hall effect sensing by having at least one magnet connected to the wheel thereof, configured for producing electric signals upon full or partial rotation of a wheel thereof caused by urine flow thereover.

17. The apparatus according to claim 16, comprising an acoustic plate configured for vibrating in response to the urine flowing thereover.

18. The apparatus according to claim 17, wherein said acoustic plate comprises an acoustic membrane.

19. The apparatus according to claim 17, wherein said acoustic plate is held in the apparatus in a tilted manner in respect to the direction of gravity to also direct the urine to flow therefrom.

20. The apparatus according to claim 17, wherein said apparatus further comprises a collecting container configured for hanging over the toilet bowl or seat, said collecting container allows collecting urine for at least one of improving acoustics of the acoustic plate and quantitative measuring-thereof.

21. The apparatus according to claim 20, wherein said container comprises an indicator for indicating a measure related to the volume of the urine therein.

22. The apparatus according to claim 17, wherein said apparatus comprises at least one holder for hanging over a toilet bowl or toilet seat.

23. The apparatus according to claim 17, comprising:
a) a body configured for hanging over a toilet seat or bowl;
b) a mechanical sensing device for mechanically measuring at least one of urine flow and urine quantity, said body being configured to direct urine therefrom into said mechanical sensing device; and
c) at least one means for producing electromagnetic signals indicative of the measured flow or quantity during a urination session, wherein said apparatus is configured such as to mechanically produce an electromagnetic signal indicative of a known quantity of urine whenever such quantity is measured thereby.

24. The apparatus according to claim 17 comprising a transducer sensor and plate attached thereto configure for sensing urination related vibrations and transforming these vibrations into electronic signals.

25. The apparatus according to claim 17, said apparatus being configured to measure or calculate at least one of the following parameters: urination flow rate, urination volume, urination flow rate changes through time based on at least one of produced acoustic and electromagnetic signals depending on the type and configuration of the apparatus being used.

26. An apparatus of claim 17, wherein the determining of at least one said parameter includes identifying urination flow rate behavior pattern based on at least one of produced acoustic and electromagnetic signal.

27. A system for determining or measuring at least one parameter related to urination of an individual, said system comprising:
a) an apparatus characterized by being configured to produce improved acoustic signals indicative of said at least one urination measure upon having urine applied thereover, said apparatus comprising a mechanical sensing device, said mechanical sensing device comprising a paddlewheel sensor based on Hall effect sensing by having at least one magnet connected to the wheel thereof, configured for producing electric signals upon full or partial rotation of a wheel thereof caused by urine flow thereover; and
b) an application module operable via an end device, said application module being configured to detect acoustic signals originating from said apparatus and calculate said at least one measure related to at least one of urine flow and urine quantity therefrom, wherein said application is adapted to use acoustic sensing means and processing means of the end device via which it operates,
wherein the determining of at least one parameter includes identifying urination flow rate behavior based on at least one of produced acoustic and electromagnetic signals.

28. The system according to claim 27, said application module further being configured to record the acoustic signals for offline processing thereof.

29. The system according to claim 27, said application module being configured to measure or calculate at least one of the following parameters: urination flow rate, urination volume, urination flow rate changes through time based on at least one of produced acoustic and electromagnetic signals depending on the type and configuration of the apparatus being used.

30. The system according to claim 27, said application module comprises a user interface allowing individuals to define beginning and ending urination.

* * * * *